(12) United States Patent
Lawrenson et al.

(10) Patent No.: US 11,576,555 B2
(45) Date of Patent: Feb. 14, 2023

(54) MEDICAL IMAGING SYSTEM, METHOD, AND COMPUTER PROGRAM

(71) Applicant: Sony Corporation, Tokyo (JP)

(72) Inventors: Matthew Lawrenson, Lausanne (CH); Shigeru Mitarai, Tokyo (JP)

(73) Assignee: SONY CORPORATION, Tokyo (JP)

( * ) Notice: Subject to any disclaimer, the term of this patent is extended or adjusted under 35 U.S.C. 154(b) by 686 days.

(21) Appl. No.: 16/495,110

(22) PCT Filed: Feb. 23, 2018

(86) PCT No.: PCT/JP2018/006743
§ 371 (c)(1),
(2) Date: Sep. 18, 2019

(87) PCT Pub. No.: WO2018/180079
PCT Pub. Date: Oct. 4, 2018

(65) Prior Publication Data
US 2021/0401301 A1    Dec. 30, 2021

(30) Foreign Application Priority Data

Mar. 29, 2017  (EP) .................................... 17163670

(51) Int. Cl.
*A61B 1/00* (2006.01)
*A61N 5/067* (2006.01)
(Continued)

(52) U.S. Cl.
CPC ........ *A61B 1/00009* (2013.01); *A61B 1/0005* (2013.01); *A61B 1/04* (2013.01);
(Continued)

(58) Field of Classification Search
CPC ..... A61B 1/00009; A61B 1/0005; A61B 1/04; A61B 5/0086; A61B 5/02042;
(Continued)

(56) References Cited

U.S. PATENT DOCUMENTS 4,746,211 A     5/1988  Ruth
2005/0065436 A1*  3/2005  Ho .................... A61B 5/0086
                                                600/431
(Continued)

FOREIGN PATENT DOCUMENTS

CN    102885605 A    1/2013
CN    104736042 A    6/2015
(Continued)

OTHER PUBLICATIONS

International Search Report and Written Opinion dated May 28, 2018 for PCT/JP2018/006743 filed on Feb. 23, 2018, 12 pages.

*Primary Examiner* — Dramos Kalapodas
(74) *Attorney, Agent, or Firm* — Xsensus LLP

(57) ABSTRACT

A medical imaging system is described that comprises an heating element configured to apply at least one heating pattern element to a material to locally heat the material; a sensor configured to capture the position of the heated material a predetermined time after the application of the heating pattern element; and circuitry configured to determine the change of the heating pattern applied to the material based upon the captured position of the heated material after the predetermined time.

21 Claims, 21 Drawing Sheets

(51) Int. Cl.
*A61B 1/04* (2006.01)
*A61B 5/02* (2006.01)
*A61B 5/026* (2006.01)
*A61B 5/028* (2006.01)
*A61F 7/12* (2006.01)
*A61B 5/00* (2006.01)
*A61N 5/06* (2006.01)

(52) U.S. Cl.
CPC ............ *A61B 5/0086* (2013.01); *A61B 5/028* (2013.01); *A61B 5/02042* (2013.01); *A61B 5/0261* (2013.01); *A61F 7/12* (2013.01); *A61N 5/067* (2021.08); *A61F 2007/126* (2013.01); *A61N 2005/0659* (2013.01); *A61N 2005/0662* (2013.01)

(58) Field of Classification Search
CPC . A61B 5/0261; A61B 5/028; A61B 1/000095; A61B 1/00097; A61B 1/046; A61B 5/0084; A61B 1/045; A61B 1/05; A61B 1/0638; A61B 1/0655; A61B 1/0684; A61B 1/043; A61B 1/00045; A61B 1/00006; A61F 7/12; A61F 2007/126; A61N 5/067; A61N 2005/0659; A61N 2005/0662

See application file for complete search history.

(56) References Cited

U.S. PATENT DOCUMENTS

| | | | |
|---|---|---|---|
| 2007/0106157 A1* | 5/2007 | Kaczkowski | A61B 8/587 600/438 |
| 2009/0177098 A1 | 7/2009 | Yakubo | |
| 2012/0265041 A1 | 10/2012 | Yamaguchi | |
| 2016/0249811 A1* | 9/2016 | Khan | A61B 1/3132 600/474 |
| 2017/0000392 A1* | 1/2017 | Smith | A61B 5/0077 |
| 2017/0042414 A1* | 2/2017 | Ito | A61B 1/00009 |

FOREIGN PATENT DOCUMENTS

| | | |
|---|---|---|
| JP | S62-298333 A | 12/1987 |
| JP | 2017-006337 A | 1/2017 |
| JP | 2017-6337 A | 1/2017 |

* cited by examiner

FIG. 4

| PATTERN 502 | MATERIAL 504 | TIME TO TRACK(s) 506 | INTENSITY 508 | DURATION(ms) 510 |
|---|---|---|---|---|
| 1st PATTERN | BLOOD | 1 | LOW | 370 |
| | | | MEDIUM | 250 |
| | | | HIGH | 150 |
| | MUSCLE | 2 | LOW | 560 |
| | | | MIL | 300 |
| | ORGAN | 3 | MEDIUM | 220 |
| | | ... | ... | ... |
| | ... | ... | ... | ... |
| 2nd PATTERN | | | ... | ... |
| | | | ... | ... |

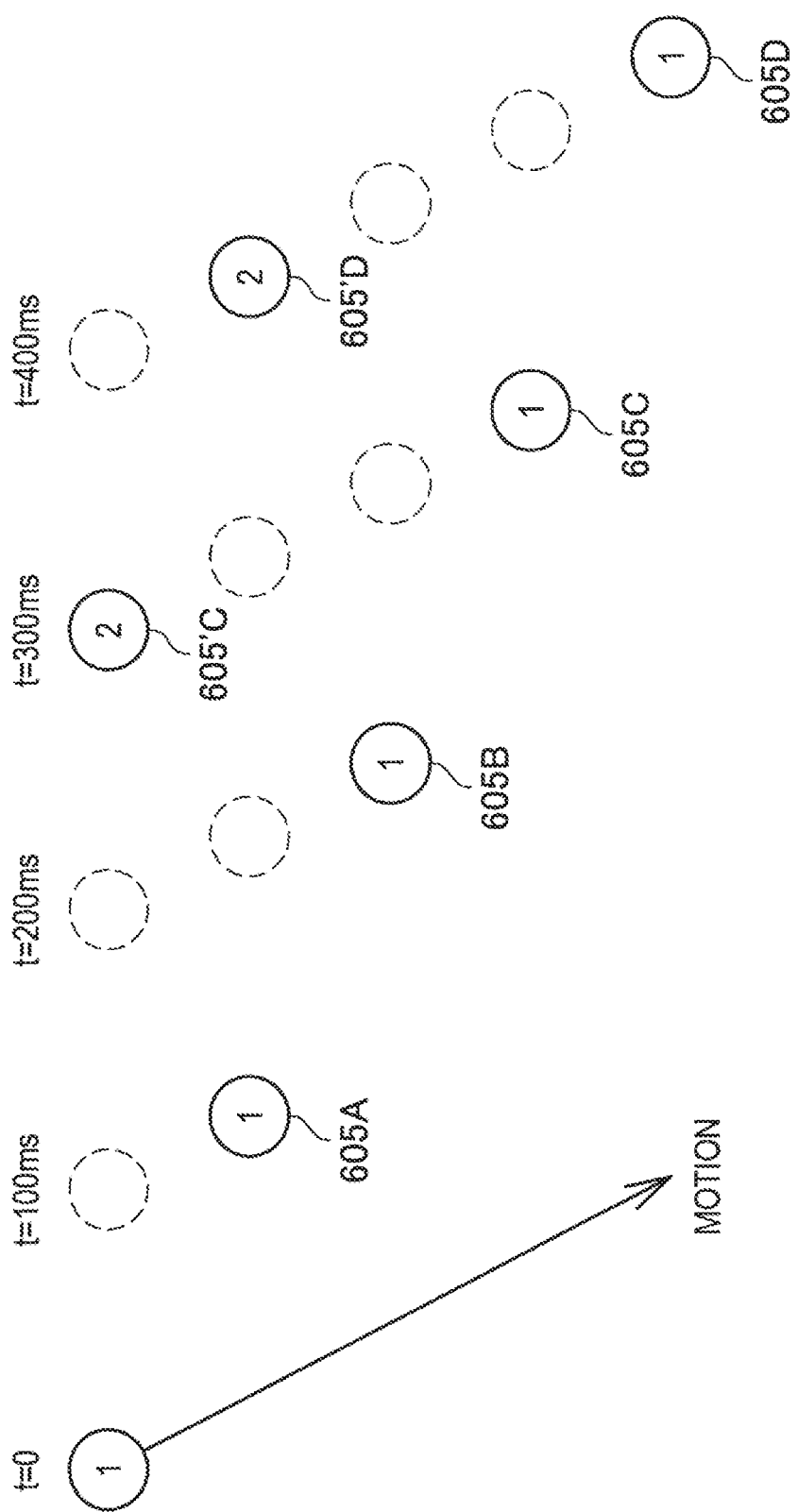

SLU MOVES AND DISPERSES

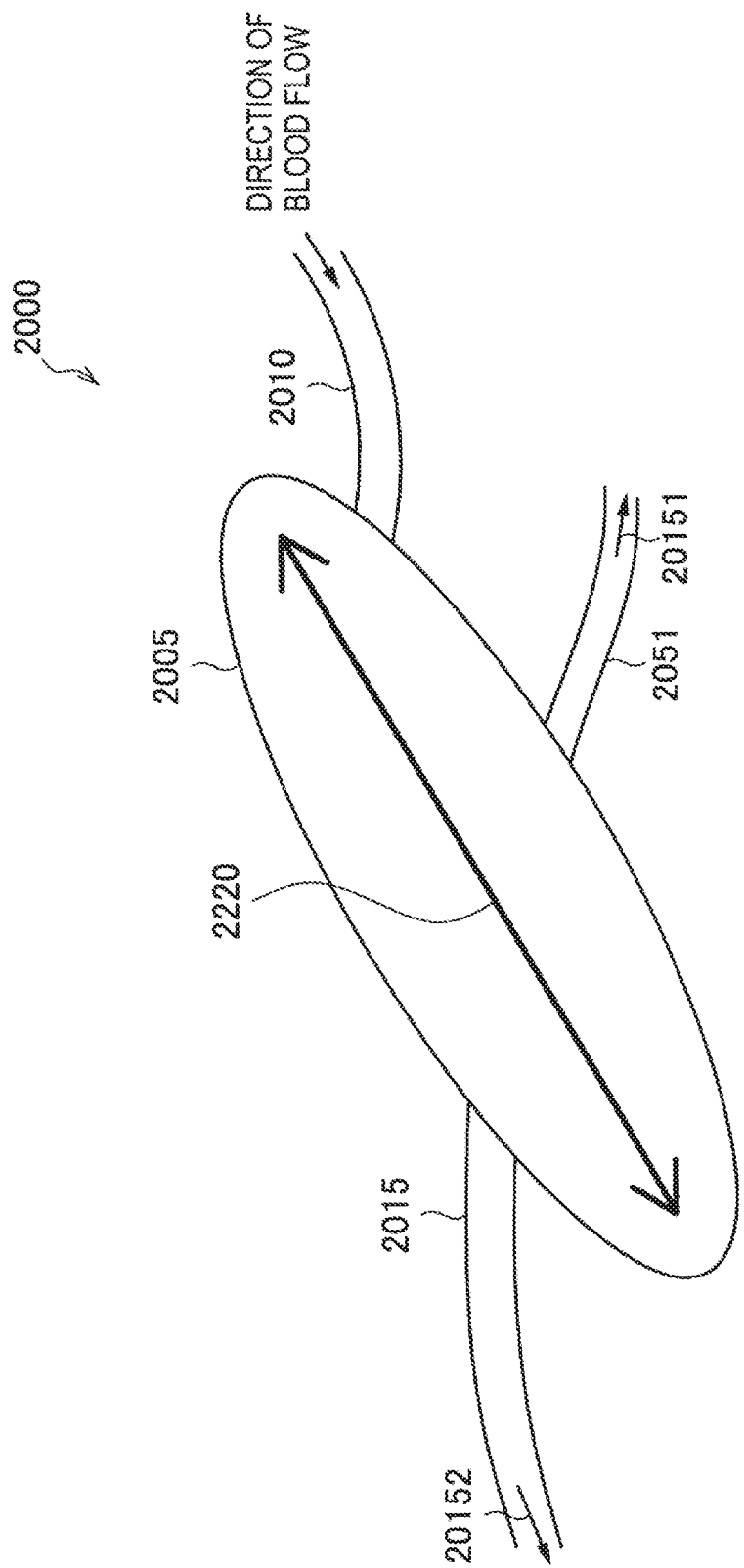

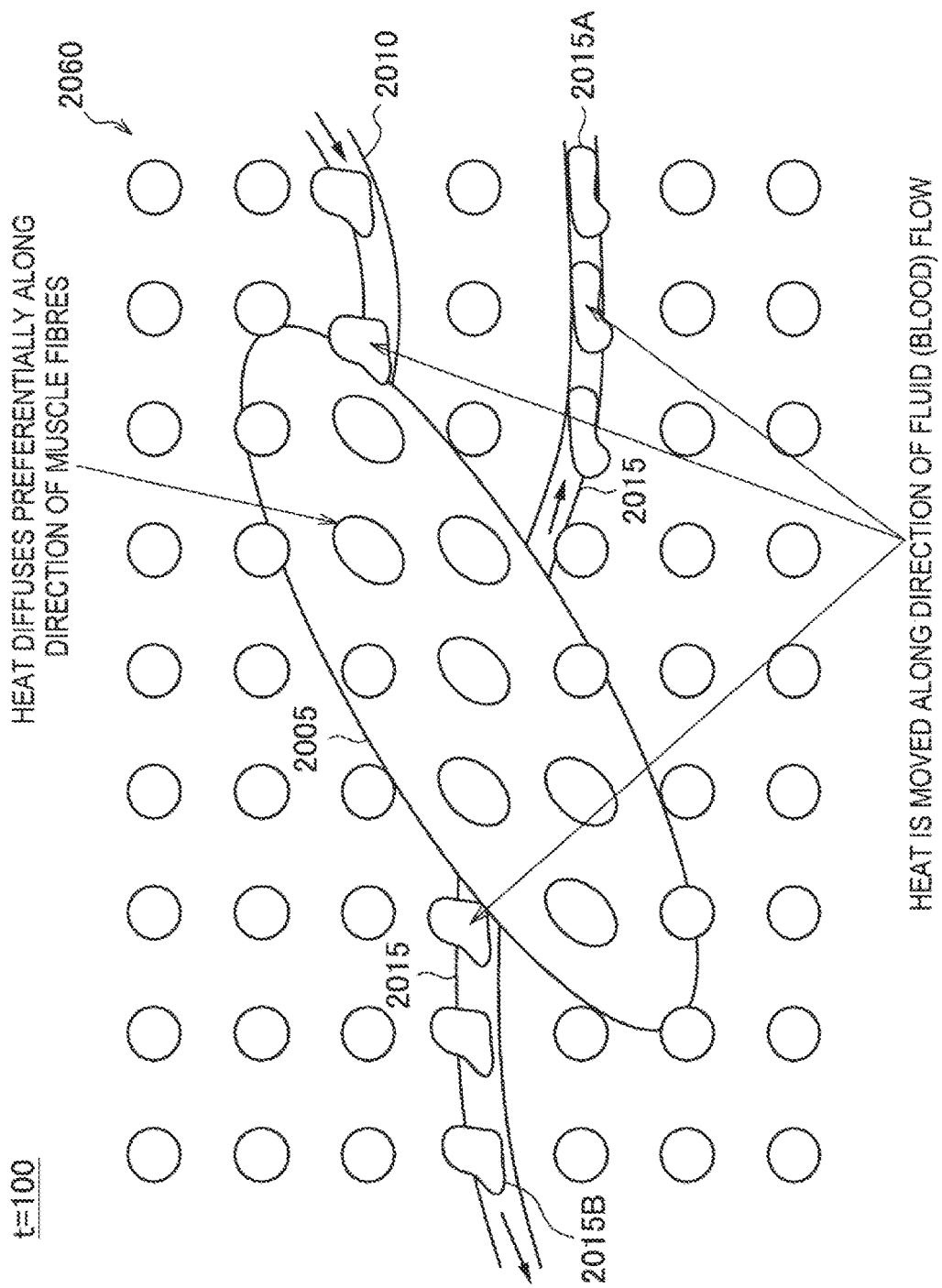

MEDICAL IMAGING SYSTEM, METHOD, AND COMPUTER PROGRAM

CROSS REFERENCE TO RELATED APPLICATIONS

The present application is based on PCT filing PCT/JP2018/006743, filed Feb. 23, 2018, which claims priority to EP 17163670.7, filed Mar. 29, 2017, the entire contents of each are incorporated herein by reference.

TECHNICAL FIELD

The present disclosure relates to a medical imaging system, method, and computer program.

BACKGROUND ART

The "background" description provided herein is for the purpose of generally presenting the context of the disclosure. Work of the presently named inventors, to the extent it is described in the background section, as well as aspects of the description which may not otherwise qualify as prior art at the time of filing, are neither expressly or impliedly admitted as prior art against the present disclosure.

A problem when performing endoscopy (such as medical endoscopy or industrial endoscopy) is to identify the source of fluid leakage. In the field of medical endoscopy, for example, there may be a wound which is the source of internal bleeding, or in industrial endoscopy, there may be a fracture in the pipe causing a fluid to leak.

Depending on the severity of the wound or fracture, finding the source of the leak may be time critical. Therefore, it is an aim of the present disclosure to assist in finding the source of a leak in endoscopy.

Additionally, where many different materials exist in the endoscopy environment, it is desirable to determine the presence and identity of the different materials. It is another aim of the present disclosure to assist in determining the presence and identity of different materials in endoscopy.

CITATION LIST

Non Patent Literature

[NPL 1] 'Contextual Point Matching for Video Stabilization', Meng, et al., NSF Prism Grant DMS-0928427
[NPL 2] 'Digital Video Stabilization and Rolling Shutter Correction Using Gyroscopes', Karpenko et al., Stanford Tech Report CTSR 2011-03.
[NPL 3] 'Video Stabilization Based on a 3D Perspective Camera Model', Zhang et al., Vis Comput DOI 10.1007/s00371-009-0310-z

SUMMARY

A medical imaging system comprising an heating element configured to apply at least one heating pattern element to a material to locally heat the material; a sensor configured to capture the position of the heated material a predetermined time after the application of the heating pattern element; and circuitry configured to determine the change of the heating pattern applied to the material based upon the captured position of the heated material after the predetermined time.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF DRAWINGS

A more complete appreciation of the disclosure and many of the attendant advantages thereof will be readily obtained as the same becomes better understood by reference to the following detailed description when considered in connection with the accompanying drawings.

FIG. 4 shows a table stored in the storage of FIG. 1 or 2.

FIG. 5 shows schematically the movement of material.

FIG. 16A to 16C shows a schematic diagram explaining material differentiation using heating patterns.

FIG. 16A to 16C shows a schematic diagram explaining material differentiation using heating patterns.

FIG. 16A to 16C shows a schematic diagram explaining material differentiation using heating patterns.

DESCRIPTION OF EMBODIMENTS

Figure 1:
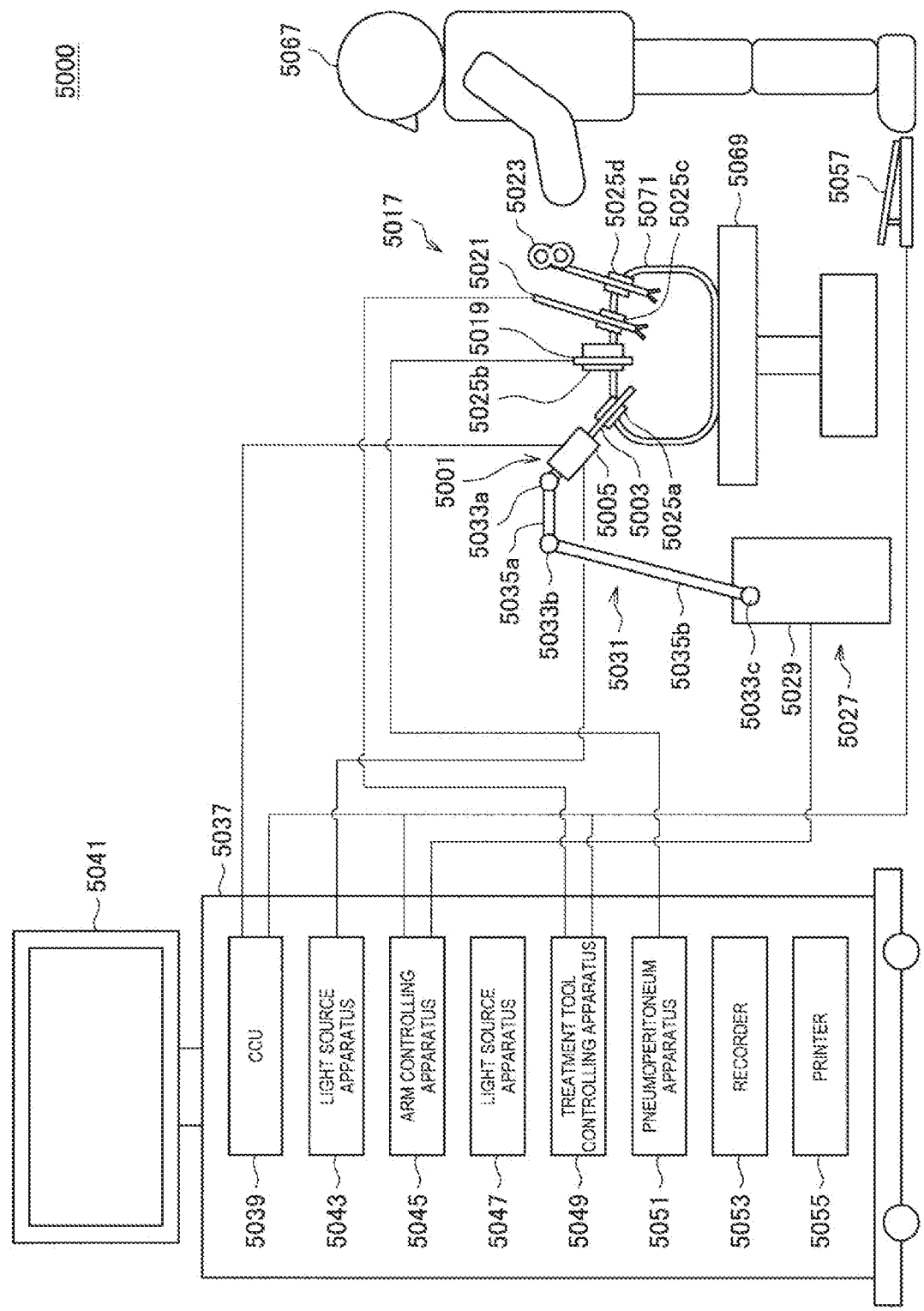
FIG. 1 is a view depicting an example of a schematic configuration of an endoscopic surgery system.

Referring now to the drawings, wherein like reference numerals designate identical or corresponding parts throughout the several views.

4. Application

<<4. Application>>

The technology according to an embodiment of the present disclosure can be applied to various products. For example, the technology according to an embodiment of the present disclosure may be applied to an endoscopic surgery system, surgical microscopy or medical imaging system or other kind of industrial endoscopy in, say pipe or tube laying or fault finding.

FIG. 1 is a view depicting an example of a schematic configuration of an endoscopic surgery system 5000 to which the technology according to an embodiment of the present disclosure can be applied. In FIG. 1, a state is illustrated in which a surgeon (medical doctor) 5067 is using the endoscopic surgery system 5000 to perform surgery for a patient 5071 on a patient bed 5069. As depicted, the endoscopic surgery system 5000 includes an endoscope 5001, other surgical tools 5017, a supporting arm apparatus 5027 which supports the endoscope 5001 thereon, and a cart 5037 on which various apparatus for endoscopic surgery are mounted.

In endoscopic surgery, in place of incision of the abdominal wall to perform laparotomy, a plurality of tubular aperture devices called trocars 5025a to 5025d are used to puncture the abdominal wall. Then, a lens barrel 5003 of the endoscope 5001 and the other surgical tools 5017 are inserted into body lumens of the patient 5071 through the trocars 5025a to 5025d. In the example depicted, as the other surgical tools 5017, a pneumoperitoneum tube 5019, an energy treatment tool 5021 and forceps 5023 are inserted into body lumens of the patient 5071. Further, the energy treatment tool 5021 is a treatment tool for performing incision and peeling of a tissue, sealing of a blood vessel or the like by high frequency current or ultrasonic vibration. However, the surgical tools 5017 depicted are mere examples at all, and as the surgical tools 5017, various surgical tools which are generally used in endoscopic surgery such as, for example, a pair of tweezers or a retractor may be used.

An image of a surgical region in a body lumen of the patient 5071 imaged by the endoscope 5001 is displayed on a display apparatus 5041. The surgeon 5067 would use the energy treatment tool 5021 or the forceps 5023 while watching the image of the surgical region displayed on the display apparatus 5041 on the real time basis to perform such treatment as, for example, resection of an affected area. It is to be noted that, though not depicted, the pneumoperitoneum tube 5019, the energy treatment tool 5021 and the forceps 5023 are supported by the surgeon 5067, an assistant or the like during surgery.

(Supporting Arm Apparatus)

The supporting arm apparatus 5027 includes an arm unit 5031 extending from a base unit 5029. In the example depicted, the arm unit 5031 includes joint portions 5033a, 5033b and 5033c and links 5035a and 5035b and is driven under the control of an arm controlling apparatus 5045. The endoscope 5001 is supported by the arm unit 5031 such that the position and the posture of the endoscope 5001 are controlled. Consequently, stable fixation in position of the endoscope 5001 can be implemented.

(Endoscope)

The endoscope 5001 includes the lens barrel 5003 which has a region of a predetermined length from a distal end thereof to be inserted into a body lumen of the patient 5071, and a camera head 5005 connected to a proximal end of the lens barrel 5003. In the example depicted, the endoscope 5001 is depicted which includes as a hard mirror having the lens barrel 5003 of the hard type. However, the endoscope 5001 may otherwise be configured as a soft mirror having the lens barrel 5003 of the soft type.

The lens barrel 5003 has, at a distal end thereof, an opening in which an objective lens is fitted. A light source apparatus 5043 is connected to the endoscope 5001 such that light generated by the light source apparatus 5043 is introduced to a distal end of the lens barrel by a light guide extending in the inside of the lens barrel 5003 and is irradiated toward an observation target in a body lumen of the patient 5071 through the objective lens. It is to be noted that the endoscope 5001 may be a direct view mirror or may be a perspective view mirror or a side view mirror.

An optical system and an image pickup element are provided in the inside of the camera head 5005 such that reflected light (observation light) from an observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 5039. It is to be noted that the camera head 5005 has a function incorporated therein for suitably driving the optical system of the camera head 5005 to adjust the magnification and the focal distance.

It is to be noted that, in order to establish compatibility with, for example, a stereoscopic vision (three dimensional (3D) display), a plurality of image pickup elements may be provided on the camera head 5005. In this case, a plurality of relay optical systems are provided in the inside of the lens barrel 5003 in order to guide observation light to each of the plurality of image pickup elements.

(Various Apparatus Incorporated in Cart)

The CCU 5039 includes a central processing unit (CPU), a graphics processing unit (GPU) or the like and integrally controls operation of the endoscope 5001 and the display apparatus 5041. In particular, the CCU 5039 performs, for an image signal received from the camera head 5005, various image processes for displaying an image based on the image signal such as, for example, a development process (demosaic process). The CCU 5039 provides the image signal for which the image processes have been performed to the display apparatus 5041. Further, the CCU 5039 transmits a control signal to the camera head 5005 to control driving of the camera head 5005. The control signal may include information relating to an image pickup condition such as a magnification or a focal distance.

The display apparatus 5041 displays an image based on an image signal for which the image processes have been performed by the CCU 5039 under the control of the CCU 5039. If the endoscope 5001 is ready for imaging of a high resolution such as 4K (horizontal pixel number 3840×vertical pixel number 2160), 8K (horizontal pixel number 7680×vertical pixel number 4320) or the like and/or ready for 3D display, then a display apparatus by which corresponding display of the high resolution and/or 3D display are possible may be used as the display apparatus 5041. Where the apparatus is ready for imaging of a high resolution such as 4K or 8K, if the display apparatus used as the display apparatus 5041 has a size of equal to or not less than 55 inches, then a more immersive experience can be obtained. Further, a plurality of display apparatus 5041 having different resolutions and/or different sizes may be provided in accordance with purposes.

The light source apparatus 5043 includes a light source such as, for example, a light emitting diode (LED) and supplies irradiation light for imaging of a surgical region to the endoscope 5001.

The arm controlling apparatus 5045 includes a processor such as, for example, a CPU and operates in accordance with a predetermined program to control driving of the arm unit 5031 of the supporting arm apparatus 5027 in accordance with a predetermined controlling method.

An inputting apparatus 5047 is an input interface for the endoscopic surgery system 5000. A user can perform inputting of various kinds of information or instruction inputting to the endoscopic surgery system 5000 through the inputting apparatus 5047. For example, the user would input various kinds of information relating to surgery such as physical information of a patient, information regarding a surgical procedure of the surgery and so forth through the inputting apparatus 5047. Further, the user would input, for example, an instruction to drive the arm unit 5031, an instruction to change an image pickup condition (type of irradiation light, magnification, focal distance or the like) by the endoscope 5001, an instruction to drive the energy treatment tool 5021 or the like through the inputting apparatus 5047.

The type of the inputting apparatus 5047 is not limited and may be that of any one of various known inputting apparatus. As the inputting apparatus 5047, for example, a mouse, a keyboard, a touch panel, a switch, a foot switch 5057 and/or a lever or the like may be applied. Where a touch panel is used as the inputting apparatus 5047, it may be provided on the display face of the display apparatus 5041.

Otherwise, the inputting apparatus 5047 is a device to be mounted on a user such as, for example, a glasses type wearable device or a head mounted display (HMD), and various kinds of inputting are performed in response to a gesture or a line of sight of the user detected by any of the devices mentioned. Further, the inputting apparatus 5047 includes a camera which can detect a motion of a user, and various kinds of inputting are performed in response to a gesture or a line of sight of a user detected from a video imaged by the camera. Further, the inputting apparatus 5047 includes a microphone which can collect the voice of a user, and various kinds of inputting are performed by voice collected by the microphone. By configuring the inputting apparatus 5047 such that various kinds of information can be inputted in a contactless fashion in this manner, especially a user who belongs to a clean area (for example, the surgeon 5067) can operate an apparatus belonging to an unclean area in a contactless fashion. Further, since the user can operate an apparatus without releasing a possessed surgical tool from its hand, the convenience to the user is improved.

A treatment tool controlling apparatus 5049 controls driving of the energy treatment tool 5021 for cautery or incision of a tissue, sealing of a blood vessel or the like. A pneumoperitoneum apparatus 5051 feeds gas into a body lumen of the patient 5071 through the pneumoperitoneum tube 5019 to inflate the body lumen in order to secure the field of view of the endoscope 5001 and secure the working space for the surgeon. A recorder 5053 is an apparatus capable of recording various kinds of information relating to surgery. A printer 5055 is an apparatus capable of printing various kinds of information relating to surgery in various forms such as a text, an image or a graph.

In the following, especially a characteristic configuration of the endoscopic surgery system 5000 is described in more detail.

(Supporting Arm Apparatus)

The supporting arm apparatus 5027 includes the base unit 5029 serving as a base, and the arm unit 5031 extending from the base unit 5029. In the example depicted, the arm unit 5031 includes the plurality of joint portions 5033*a*, 5033*b* and 5033*c* and the plurality of links 5035*a* and 5035*b* connected to each other by the joint portion 5033*b*. In FIG. A1, for simplified illustration, the configuration of the arm unit 5031 is depicted in a simplified form. Actually, the shape, number and arrangement of the joint portions 5033*a* to 5033*c* and the links 5035*a* and 5035*b* and the direction and so forth of axes of rotation of the joint portions 5033*a* to 5033*c* can be set suitably such that the arm unit 5031 has a desired degree of freedom. For example, the arm unit 5031 may preferably be configured such that it has a degree of freedom equal to or not less than 6 degrees of freedom. This makes it possible to move the endoscope 5001 freely within the movable range of the arm unit 5031. Consequently, it becomes possible to insert the lens barrel 5003 of the endoscope 5001 from a desired direction into a body lumen of the patient 5071.

An actuator is provided in each of the joint portions 5033*a* to 5033*c*, and the joint portions 5033*a* to 5033*c* are configured such that they are rotatable around predetermined axes of rotation thereof by driving of the respective actuators. The driving of the actuators is controlled by the arm controlling apparatus 5045 to control the rotational angle of each of the joint portions 5033*a* to 5033*c* thereby to control driving of the arm unit 5031. Consequently, control of the position and the posture of the endoscope 5001 can be implemented. Thereupon, the arm controlling apparatus 5045 can control driving of the arm unit 5031 by various known controlling methods such as force control or position control.

For example, if the surgeon 5067 suitably performs operation inputting through the inputting apparatus 5047 (including the foot switch 5057), then driving of the arm unit 5031 may be controlled suitably by the arm controlling apparatus 5045 in response to the operation input to control the position and the posture of the endoscope 5001. After the endoscope 5001 at the distal end of the arm unit 5031 is moved from an arbitrary position to a different arbitrary position by the control just described, the endoscope 5001 can be supported fixedly at the position after the movement. It is to be noted that the arm unit 5031 may be operated in a master-slave fashion. In this case, the arm unit 5031 may be remotely controlled by the user through the inputting apparatus 5047 which is placed at a place remote from the surgery room.

Further, where force control is applied, the arm controlling apparatus 5045 may perform power-assisted control to drive the actuators of the joint portions 5033*a* to 5033*c* such that the arm unit 5031 may receive external force by the user and move smoothly following the external force. This makes it possible to move, when the user directly touches with and moves the arm unit 5031, the arm unit 5031 with comparatively weak force. Accordingly, it becomes possible for the user to move the endoscope 5001 more intuitively by a simpler and easier operation, and the convenience to the user can be improved.

Here, generally in endoscopic surgery, the endoscope 5001 is supported by a medical doctor called scopist. In contrast, where the supporting arm apparatus 5027 is used, the position of the endoscope 5001 can be fixed more certainly without hands, and therefore, an image of a surgical region can be obtained stably and surgery can be performed smoothly.

It is to be noted that the arm controlling apparatus 5045 may not necessarily be provided on the cart 5037. Further, the arm controlling apparatus 5045 may not necessarily be a single apparatus. For example, the arm controlling apparatus 5045 may be provided in each of the joint portions 5033a to 5033c of the arm unit 5031 of the supporting arm apparatus 5027 such that the plurality of arm controlling apparatus 5045 cooperate with each other to implement driving control of the arm unit 5031.

(Light Source Apparatus)

The light source apparatus 5043 supplies irradiation light upon imaging of a surgical region to the endoscope 5001. The light source apparatus 5043 includes a white light source which includes, for example, an LED, a laser light source or a combination of them. In this case, where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 5043. Further, in this case, if laser beams from the respective RGB laser light sources are irradiated time-divisionally on an observation target and driving of the image pickup elements of the camera head 5005 is controlled in synchronism with the irradiation timings, then images individually corresponding to the R, G and B colors can be picked up time-divisionally. According to the method just described, a color image can be obtained even if a color filter is not provided for the image pickup element.

Further, driving of the light source apparatus 5043 may be controlled such that the intensity of light to be outputted is changed for each predetermined time. By controlling driving of the image pickup element of the camera head 5005 in synchronism with the timing of the change of the intensity of light to acquire images time-divisionally and synthesizing the images, an image of a high dynamic range free from underexposed blocked up shadows and overexposed highlights can be created.

Figure 3A:
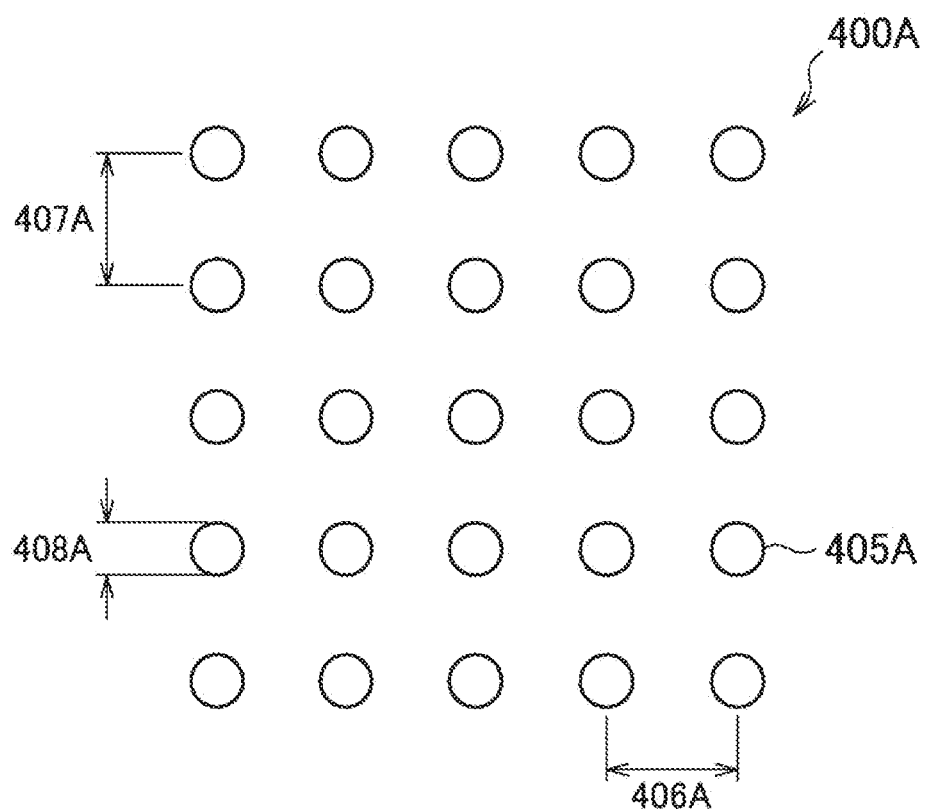
FIG. 3A to 3C shows heating patterns according to embodiments of the disclosure.
Figure 3B:
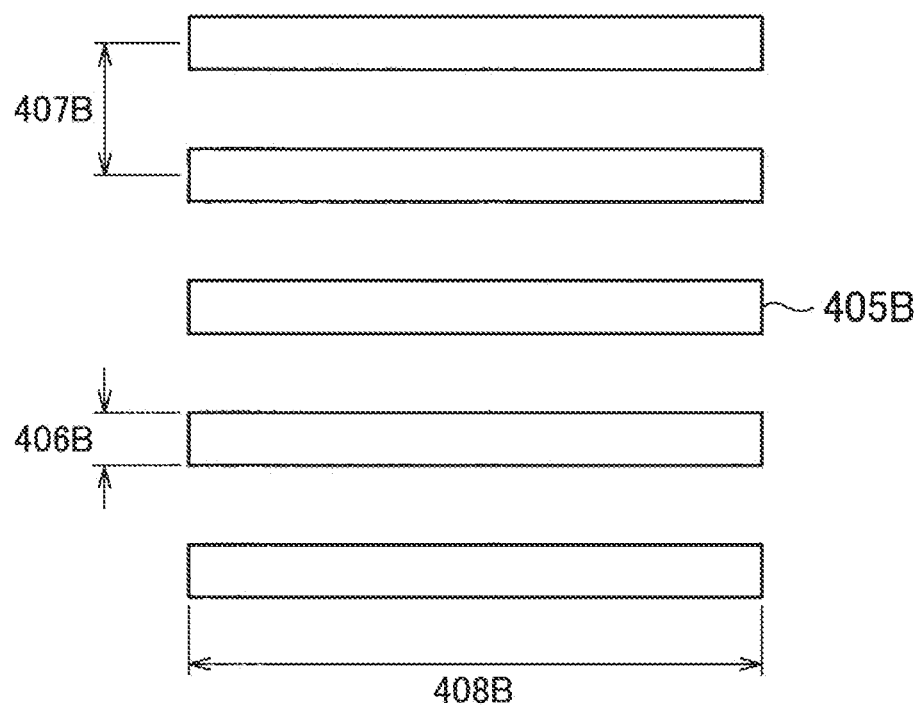
Figure 3C:
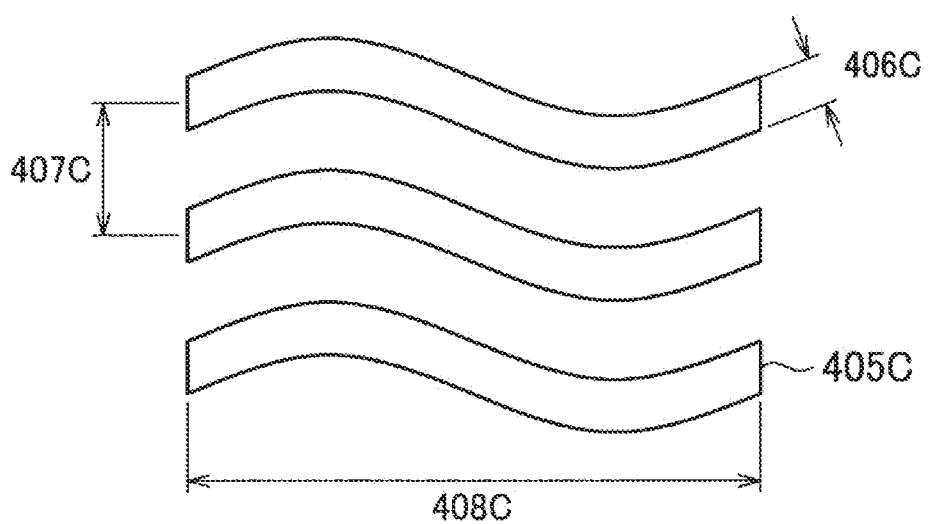

Further, the light source apparatus 5043 may be configured to supply light of a predetermined wavelength band ready for special light observation. This may include, but not be limited to laser light such as that provided by a Vertical Cavity surface laser or any kind of laser light. Alternatively or additionally, the light may be InfraRed (IR) light. In special light observation, for example, by utilizing the wavelength dependency of absorption of light in a body tissue to irradiate light of a narrower band in comparison with irradiation light upon ordinary observation (namely, white light), narrow band light observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 5043 can be configured to supply such narrowband light and/or excitation light suitable for special light observation as described above. The light source may also apply a heat pattern to an area. This heat pattern will be explained later with reference to FIGS. 3A-C. The light source apparatus 5043 is, in embodiments, a Vertical Cavity Surface-Emitting Laser (VCSEL) which can produce light in the visible part of the electromagnetic spectrum and some produce light in the Infra-Red part of the electromagnetic spectrum. In this respect, the light source apparatus 5043 may also act as a visible light source illuminating the area. The light source apparatus 5043 is configured to produce a pattern of light. These patterns are shown in FIGS. 3A to 3C.

(Camera Head and CCU)

Figure 2:
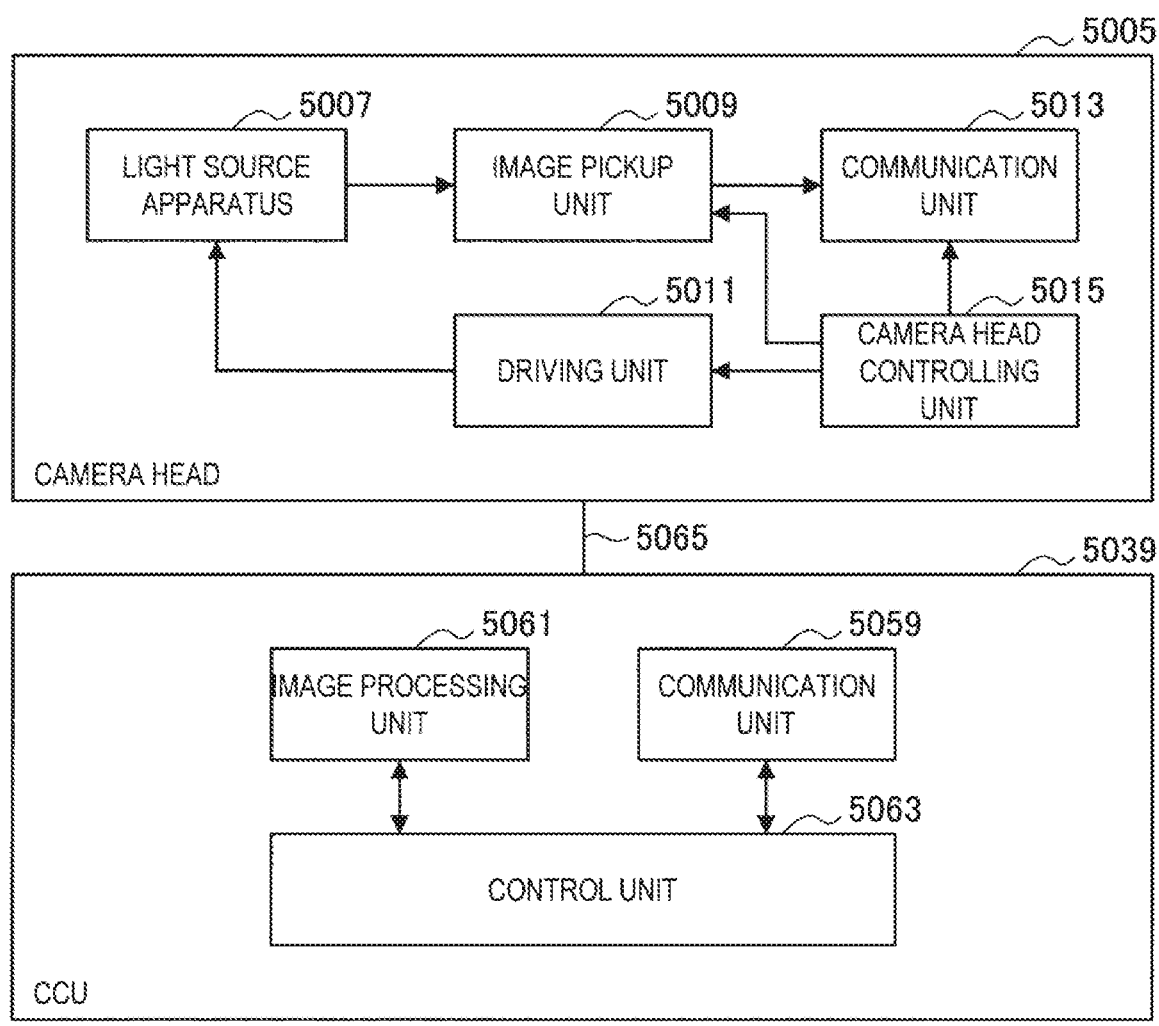
FIG. 2 is a block diagram depicting an example of a functional configuration of a camera head and a camera control unit (CCU) depicted in FIG. 1.

Functions of the camera head 5005 of the endoscope 5001 and the CCU 5039 are described in more detail with reference to FIG. 2. FIG. 2 is a block diagram depicting an example of a functional configuration of the camera head 5005 and the CCU 5039 depicted in FIG. 1.

Referring to FIG. 2, the camera head 5005 has, as functions thereof, a lens unit 5007, an image pickup unit 5009, a driving unit 5011, a communication unit 5013 and a camera head controlling unit 5015. Further, the CCU 5039 has, as functions thereof, a communication unit 5059, an image processing unit 5061 and a control unit 5063. The camera head 5005 and the CCU 5039 are connected to be bidirectionally communicable to each other by a transmission cable 5065.

First, a functional configuration of the camera head 5005 is described. The lens unit 5007 is an optical system provided at a connecting location of the camera head 5005 to the lens barrel 5003. Observation light taken in from a distal end of the lens barrel 5003 is introduced into the camera head 5005 and enters the lens unit 5007. The lens unit 5007 includes a combination of a plurality of lenses including a zoom lens and a focusing lens. The lens unit 5007 has optical properties adjusted such that the observation light is condensed on a light receiving face of the image pickup element of the image pickup unit 5009. Further, the zoom lens and the focusing lens are configured such that the positions thereof on their optical axis are movable for adjustment of the magnification and the focal point of a picked up image.

The image pickup unit 5009 includes an image pickup element and disposed at a succeeding stage to the lens unit 5007. Observation light having passed through the lens unit 5007 is condensed on the light receiving face of the image pickup element, and an image signal corresponding to the observation image is generated by photoelectric conversion of the image pickup element. The image signal generated by the image pickup unit 5009 is provided to the communication unit 5013.

As the image pickup element which is included by the image pickup unit 5009, an image sensor, for example, of the complementary metal oxide semiconductor (CMOS) type is used which has a Bayer array and is capable of picking up an image in color. It is to be noted that, as the image pickup element, an image pickup element may be used which is ready, for example, for imaging of an image of a high resolution equal to or not less than 4K. If an image of a surgical region is obtained in a high resolution, then the surgeon 5067 can comprehend a state of the surgical region in enhanced details and can proceed with the surgery more smoothly.

Further, the image pickup element which is included by the image pickup unit 5009 includes such that it has a pair of image pickup elements for acquiring image signals for the right eye and the left eye compatible with 3D display. Where 3D display is applied, the surgeon 5067 can comprehend the depth of a living body tissue in the surgical region more accurately. It is to be noted that, if the image pickup unit 5009 is configured as that of the multi-plate type, then a plurality of systems of lens units 5007 are provided corresponding to the individual image pickup elements of the image pickup unit 5009.

The image pickup unit 5009 may not necessarily be provided on the camera head 5005. For example, the image pickup unit 5009 may be provided just behind the objective lens in the inside of the lens barrel 5003.

The driving unit 5011 includes an actuator and moves the zoom lens and the focusing lens of the lens unit 5007 by a predetermined distance along the optical axis under the control of the camera head controlling unit 5015. Consequently, the magnification and the focal point of a picked up image by the image pickup unit 5009 can be adjusted suitably.

The communication unit 5013 includes a communication apparatus for transmitting and receiving various kinds of information to and from the CCU 5039. The communication unit 5013 transmits an image signal acquired from the image pickup unit 5009 as RAW data to the CCU 5039 through the transmission cable 5065. Thereupon, in order to display a picked up image of a surgical region in low latency, preferably the image signal is transmitted by optical communication. This is because, upon surgery, the surgeon 5067 performs surgery while observing the state of an affected area through a picked up image, it is demanded for a moving image of the surgical region to be displayed on the real time basis as far as possible in order to achieve surgery with a higher degree of safety and certainty. Where optical communication is applied, a photoelectric conversion module for converting an electric signal into an optical signal is provided in the communication unit 5013. After the image signal is converted into an optical signal by the photoelectric conversion module, it is transmitted to the CCU 5039 through the transmission cable 5065.

Further, the communication unit 5013 receives a control signal for controlling driving of the camera head 5005 from the CCU 5039. The control signal includes information relating to image pickup conditions such as, for example, information that a frame rate of a picked up image is designated, information that an exposure value upon image picking up is designated and/or information that a magnification and a focal point of a picked up image are designated. The communication unit 5013 provides the received control signal to the camera head controlling unit 5015. It is to be noted that also the control signal from the CCU 5039 may be transmitted by optical communication. In this case, a photoelectric conversion module for converting an optical signal into an electric signal is provided in the communication unit 5013. After the control signal is converted into an electric signal by the photoelectric conversion module, it is provided to the camera head controlling unit 5015.

It is to be noted that the image pickup conditions such as the frame rate, exposure value, magnification or focal point are set automatically by the control unit 5063 of the CCU 5039 on the basis of an acquired image signal. In other words, an auto exposure (AE) function, an auto focus (AF) function and an auto white balance (AWB) function are incorporated in the endoscope 5001.

The camera head controlling unit 5015 controls driving of the camera head 5005 on the basis of a control signal from the CCU 5039 received through the communication unit 5013. For example, the camera head controlling unit 5015 controls driving of the image pickup element of the image pickup unit 5009 on the basis of information that a frame rate of a picked up image is designated and/or information that an exposure value upon image picking up is designated. Further, for example, the camera head controlling unit 5015 controls the driving unit 5011 to suitably move the zoom lens and the focus lens of the lens unit 5007 on the basis of information that a magnification and a focal point of a picked up image are designated. The camera head controlling unit 5015 may further include a function for storing information for identifying the lens barrel 5003 and/or the camera head 5005.

It is to be noted that, by disposing the components such as the lens unit 5007 and the image pickup unit 5009 in a sealed structure having high airtightness and waterproof, the camera head 5005 can be provided with resistance to an autoclave sterilization process.

Now, a functional configuration of the CCU 5039 is described. The communication unit 5059 includes a communication apparatus for transmitting and receiving various kinds of information to and from the camera head 5005. The communication unit 5059 receives an image signal transmitted thereto from the camera head 5005 through the transmission cable 5065. Thereupon, the image signal may be transmitted preferably by optical communication as described above. In this case, for the compatibility with optical communication, the communication unit 5059 includes a photoelectric conversion module for converting an optical signal into an electric signal. The communication unit 5059 provides the image signal after conversion into an electric signal to the image processing unit 5061.

Further, the communication unit 5059 transmits, to the camera head 5005, a control signal for controlling driving of the camera head 5005. The control signal may also be transmitted by optical communication.

The image processing unit 5061 performs various image processes for an image signal in the form of RAW data transmitted thereto from the camera head 5005. The image processes include various known signal processes such as, for example, a development process, an image quality improving process (a bandwidth enhancement process, a super-resolution process, a noise reduction (NR) process and/or an image stabilization process) and/or an enlargement process (electronic zooming process). Further, the image processing unit 5061 performs a detection process for an image signal in order to perform AE, AF and AWB.

The image processing unit 5061 includes a processor such as a CPU or a GPU, and when the processor operates in accordance with a predetermined program, the image processes and the detection process described above can be performed. It is to be noted that, where the image processing unit 5061 includes a plurality of GPUs, the image processing unit 5061 suitably divides information relating to an image signal such that image processes are performed in parallel by the plurality of GPUs.

The control unit 5063 performs various kinds of control relating to image picking up of a surgical region by the endoscope 5001 and display of the picked up image. For example, the control unit 5063 generates a control signal for controlling driving of the camera head 5005. Thereupon, if image pickup conditions are inputted by the user, then the control unit 5063 generates a control signal on the basis of the input by the user. Alternatively, where the endoscope

5001 has an AE function, an AF function and an AWB function incorporated therein, the control unit 5063 suitably calculates an optimum exposure value, focal distance and white balance in response to a result of a detection process by the image processing unit 5061 and generates a control signal.

Further, the control unit 5063 controls the display apparatus 5041 to display an image of a surgical region on the basis of an image signal for which image processes have been performed by the image processing unit 5061. Thereupon, the control unit 5063 recognizes various objects in the surgical region image using various image recognition technologies. For example, the control unit 5063 can recognize a surgical tool such as forceps, a particular living body region, bleeding, mist when the energy treatment tool 5021 is used and so forth by detecting the shape, color and so forth of edges of the objects included in the surgical region image. The control unit 5063 causes, when it controls the display unit 5041 to display a surgical region image, various kinds of surgery supporting information to be displayed in an overlapping manner with an image of the surgical region using a result of the recognition. Where surgery supporting information is displayed in an overlapping manner and presented to the surgeon 5067, the surgeon 5067 can proceed with the surgery more safety and certainty.

The transmission cable 5065 which connects the camera head 5005 and the CCU 5039 to each other is an electric signal cable ready for communication of an electric signal, an optical fiber ready for optical communication or a composite cable ready for both of electrical and optical communication.

Here, while, in the example depicted, communication is performed by wired communication using the transmission cable 5065, the communication between the camera head 5005 and the CCU 5039 may be performed otherwise by wireless communication. Where the communication between the camera head 5005 and the CCU 5039 is performed by wireless communication, there is no necessity to lay the transmission cable 5065 in the surgery room. Therefore, such a situation that movement of medical staff in the surgery room is disturbed by the transmission cable 5065 can be eliminated.

An example of the endoscopic surgery system 5000 to which the technology according to an embodiment of the present disclosure can be applied has been described above. It is to be noted here that, although the endoscopic surgery system 5000 has been described as an example, the system to which the technology according to an embodiment of the present disclosure can be applied is not limited to the example. For example, the technology according to an embodiment of the present disclosure may be applied to a soft endoscopic system for inspection or a microscopic surgery system.

The technology according to an embodiment of the present disclosure can be applied suitably to the CCU 5039 from among the components described hereinabove. Specifically, the technology according to an embodiment of the present disclosure is applied to an endoscopy system, surgical microscopy or medical imaging. By applying the technology according to an embodiment of the present disclosure to these areas, sources of leaks such as cuts can be found. This reduces the risk to the patient's safety during operations. Additionally, different materials may be identified and displayed to the surgeon. This assists in diagnosing cancerous materials which may be biopsied. This improves detection rates of cancer.

Generally, the light pattern which is imparted on the patient comprises one or more pattern elements formed from the light. These pattern elements are defined as distinct portions of light having a predefined shape and position relative to each other.

Referring to FIG. 3A, a first pattern of light 400A is shown. Specifically, the first pattern of light 400A is composed of pattern elements 405A which are dots. These dots have a defined diameter of 408A and have centres separated by 407A in the vertical direction and 406A in the horizontal direction. Typical dot spacing to achieve resolutions from fine vasculature to larger arteries would be from 100 microns to 5 mm. Suitable dot diameters would be from one tenth to one quarter of the dot spacing.

Referring to FIG. 3B, a second pattern of light 400B is shown. Specifically, the second pattern of light 400B is composed of pattern elements 405B which are, in this case, horizontal bars. Of course, the bars may be oriented vertically or diagonally. The bars have a defined length of 408B and have centres separated by 407B in the vertical direction. The thickness of each bar is shown as 406B. The light intensity within each linear bar may be uniform across the length and/or width of the bar. Alternatively, the intensity may vary across the length or width of the bar. For example, the intensity may be sinusoidal across the length and/or width of the bar.

Referring to FIG. 3C, a third pattern of light 400C is shown. Specifically, the third pattern of light 400C is composed of pattern elements 405C which are sinusoidal shaped bars having a defined period. The sinusoidal shaped bars have a defined period of 408C and have centres separated by 407C in the vertical direction. The thickness of each bar is shown as 406C.

The determination of the shape of pattern of light to be used may be made by the endoscope operator or the CCU 5039. Factors which influence the shape of pattern may include the size of the area to be heated, the shape of the area to be heated and/or the amount of heat to be applied to the material.

Specifically, in one example, for a material requiring high levels of heating, the pattern of FIG. 3B may be selected. This is because the amount of light imparted onto the material is higher than the pattern of FIG. 3A. Other factors such as shape of material to be heated may also influence the determination of the pattern to be used.

In order to create the light pattern, the light source apparatus 5047 may contain an array of elements, each element creating a corresponding pattern element. For example, the light source apparatus 5047 may include VCSEL elements with a structured distribution across the VCSEL array.

The light source apparatus 5047 may include a diffractive optical element overlaid on the light source 315 to impart the required pattern on the projected light from the light source apparatus 5047.

The light source apparatus 5047 may scan the pattern on the patient by modulating the light emitted from the light source apparatus 5047 and directing the light using a MEMs actuated mirror.

The purpose of the light source apparatus 5047 is to provide heat to a localised area. This is achieved by the provision of Infra-Red light on the pattern element. The size and shape of the pattern element is predetermined and so the localised area which is heated is defined.

As the size and shape of the pattern element is defined, the heat applied to the localised area will be determined by the intensity of the infra-red light and the time for which the infra-red light is applied to the patient. For any given material upon which the infra-red light is applied, this will increase the temperature of the material by a defined amount. By tracking the size and the movement of heated area of material, the displacement of the material and even the material itself may be determined.

As will be explained later, the pattern of infra-red light, the intensity and duration of the applied infra-red light and the material upon which the infra-red light is applied will be stored in a table as set out in FIG. 5.

Referring to FIG. 4, a table 500 is shown. The table 500 is stored in storage located in the CCU 5039 in embodiments. Of course, the table 500 may instead be stored a location on a network.

The table 500 stores details of each of the first, second and third patterns. These are stored in column 502. Associated with each pattern is a material column 504. These materials are found within a patient. Although only three materials found in the patient (blood, muscle, organ) are detailed in the material column, more or less materials may be defined. Further, other categories of material found within the patient may be defined. For example, different organs, cartilage, sinew or the like may be defined.

The table 500 also includes a column 506 which is the time for which the heat must be detected on the material. This allows the displacement of the material over that period of time to be measured. In this instance, included within column 506 is a choice of 1, 2 or 3 seconds over which the displacement of the material is to be tracked. Over course, longer, shorter or different times to those in column 506 are envisaged.

The table includes a column 508 which is the intensity of the applied heat. This intensity will vary depending upon the area in which the heat is to be applied. In sensitive areas within the patient, a low intensity heat is more appropriate to avoid damage to the material. However, in areas which are subject to movement, a high intensity heat may be appropriate so that the heat is applied to a very specific area of the material over a short period of time to reduce the impact of movement.

The table includes a column 510 which is the duration. This column is the time duration for which the Infra-Red light (heat) is applied to the material using the desired intensity and pattern. It is envisaged that the endoscope operator will select the pattern type, the material, the time to track the displacement and the intensity and based upon this user selected criteria, the correct duration for which the infra-red light (heat) must be applied to the material is chosen. The CCU 5039 then controls the light source apparatus 5047 to apply the infra-red light to the material using the appropriate pattern, the desired intensity and the appropriate duration.

Although not shown in the table 500, it is envisaged that a flow per unit time will be stored in association with the material. This value is particularly useful where the material is blood. Specifically, in embodiments, the flow per unit time will be stored in association with blood and indicates the amount of movement of the blood per unit time from a cut of a unit size at a certain part of a human body. This is because blood flow from a cut at a certain part of the patient is consistent between patients for any given size of cut. In other words, the blood flow from a cut at a certain part of the patient, per unit area of cut, is generally consistent between patients (unless a larger artery has been cut). As will be explained later, this flow rate value will be used to establish the source of the cut.

Of course, although the above mentions the flow rate of blood, the disclosure is not so limited and may apply to any fluid in either the medical or industrial fields.

It is envisaged that the table 500 will be pre-populated at the time of manufacture and the respective durations will be determined during clinical trials.

The table mentioned in FIG. 5 is for a single pulse of infra-red light. However, it is envisaged that the infra-red light will be pulsed at regular intervals. For example, where the material is stationary, the interval between pulses of infra-red light may be longer than where the material is moving quickly. This is because the material will displace more if the movement of the material is high. Consequently, the interval between pulses may be selected depending upon the movement of the material. For example, if the operator of the endoscope wishes to determine the location of a large cut (where blood is flowing rapidly) within the patient, the interval between consecutive pulses may be set at 100 ms. However, where the operator of the endoscope wishes to find the source of a very small cut (where blood is flowing very slowly) within the patient, the interval between consecutive pulses may be set at 300 ms.

Although the above mentions the operator of the endoscope selecting the time between each pulse, the disclosure is not so limited. For example, the CCU 5039 may be used to automatically determine the time between consecutive pulses.

There will now be described several example embodiments for illustration.

Firstly, there will be described the case where the heated area on the material moves. This occurs, for example, with organs during respiration. Secondly, there will be described the case where the material disperses and moves and disperses. This occurs, for example, when a cut occurs and the blood flow from the cut is to be tracked.

Referring to FIG. 4, the movement of the heated material is shown. Specifically, in the diagram of FIG. 5, at time, t=0, the first pattern 400A of infra-red light is shone onto the material. For example, the first pattern 400A of infra-red light is shone onto the material for 150 ms at high intensity. This heats the material to a particular temperature. The CCU 5039 captures the image of the heated material at this point using an infra-red image sensor located in the image pickup unit 5009.

At time, t=100 ms, the heated area of material moves to a new position 605A identified by the solid circular line. The CCU 5039 captures the image of the heated material at this point using the infra-red image sensor.

Similarly, at time, t=200 ms, the heated area of material moves to a new positon 605B identified by the solid circular line. The CCU 5039 captures the image of the heated material at this point using the infra-red image sensor.

At time, t=300 ms, the heated area of material moves to a new position 605C identified by the solid circular line. Additionally, the light source apparatus 5047 reapplies the first pattern 400A to the material at the original location for 150 ms at high intensity. In other words, the material at the original location is heated to the desired temperature. This is shown as 605'C in FIG. 5. The CCU 5039 captures the image of the heated material at this point using the infra-red image sensor.

At time, t=400 ms, the first area of heated material moves to 605D and the second (later) area of heated material moved to 605'D. The CCU 5039 captures the image of the heated material at this point using the infra-red image sensor.

Figure 7:
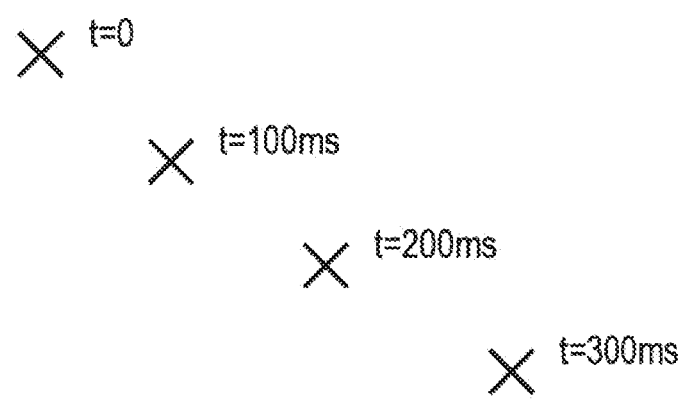
FIGS. 7 and 8 show further representations of the movement of material.
Figure 8:
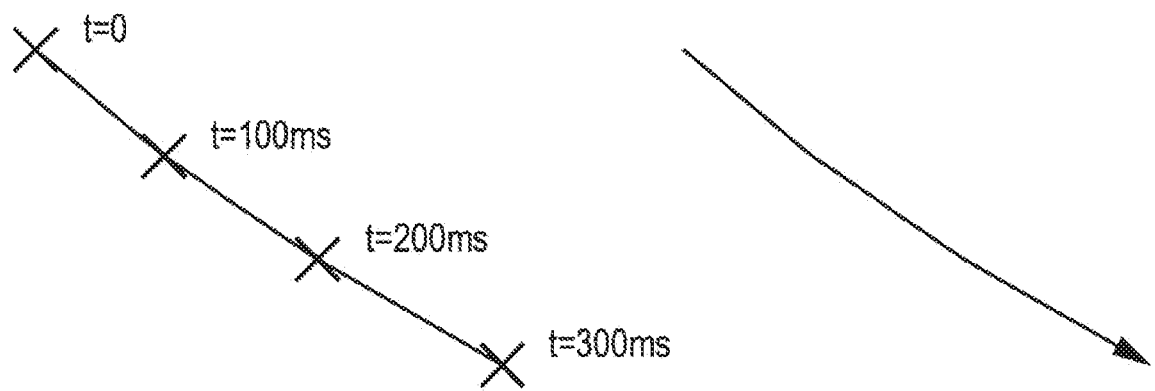

As the images are captured every 100 ms, FIG. 7 shows the position of the centre of the heated material during the time, t=0, 100 ms, 200 ms and 300 ms shown in FIG. 5. FIG. 8 shows these positions with a connecting line drawn. As will be apparent from FIG. 8, with the infra-red image being periodically captured (in this case, every 100 ms), the connecting line shows the direction of movement of the heated material.

Referring back to the second case where the material moves and disperses, reference is made to FIG. 6. In diagram (A), the movement of heated material with no dispersion is shown. This is similar to the description of FIGS. 5, 7 and 8 and so will not be described any further for brevity.

In diagram (B), the heated material does not move, but instead the heated material disperses. This kind of behaviour is exhibited where there is a small bleed (such as caused by a hole). In other words, the amount of blood flowing from the hole is small so that it pools around the cut rather than flows from the cut. Specifically, in the diagram of FIG. 6(B), at time, t=0, the first pattern 400A of infra-red light is shone onto the material. For example, the first pattern 400A of infra-red light is shone onto the material for 150 ms at high intensity. This heats the material to a particular temperature. The CCU 5039 captures the image of the heated material at this point using the infra-red image sensor.

At time, t=100 ms, the heated material disperses around the initial position. In other words, the heated material has not moved, but it has dispersed around the initial heating position. The CCU 5039 captures the image of the heated material at this point using the infra-red image sensor.

Similarly, at time, t=200 ms, the heated material continues to disperse around the initial position. The CCU 5039 captures the image of the heated material at this point using the infra-red image sensor.

In diagram (C), a simplified diagram showing the heated material moving and dispersing is provided. This kind of behaviour is exhibited where there is a large bleed (such as a haemorrhage). In other words, the amount of blood flowing from the haemorrhage is large so that the blood moves and disperses at the same time.

Figure 6A:
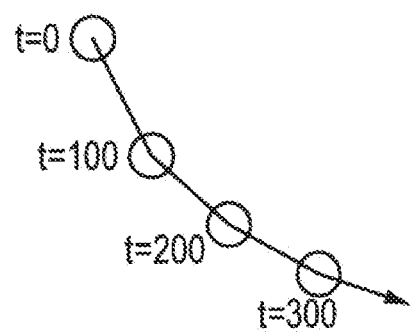
FIG. 6A to 6E shows schematically the movement and dispersal of material.
Figure 6B:
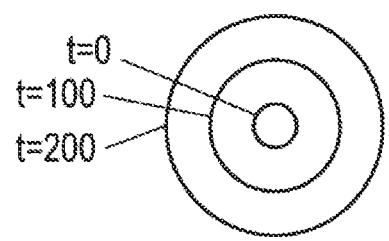
Figure 6C:
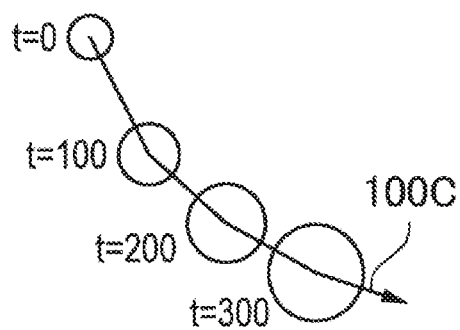

In the diagram of FIG. 6(C), at time, t=0, the first pattern 400A of infra-red light is shone onto the material. For example, the first pattern 400A of infra-red light is shone onto the material for 150 ms at high intensity. This heats the material to a particular temperature. The CCU 5039 captures the image of the heated material at this point using the infra-red image sensor.

At time, t=100 ms, the heated material has moved and dispersed along a line of movement 700C. The CCU 5039 captures the image of the heated material at this point using the infra-red image sensor.

At time, t=200 ms, the heated material has again moved and dispersed along the line of movement 700C. The CCU 5039 captures the image of the heated material at this point using the infra-red image sensor.

At time, t=300 ms, the heated material has moved further along the line of movement 700C and has dispersed more. The CCU 5039 captures the image of the heated material at this point using the infra-red image sensor.

From the arrow drawn in FIG. 6(C), the path of the heated material can be seen.

Figure 9:
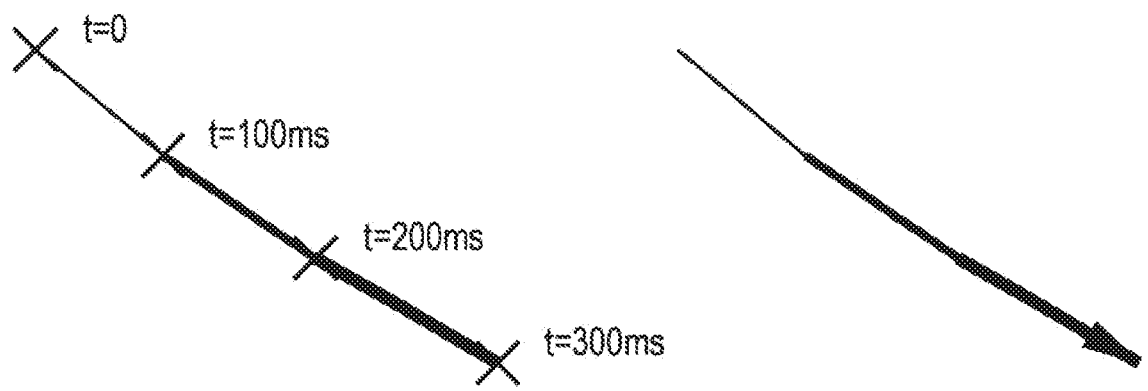
FIG. 9 shows further representations of the dispersal of material.

Although FIG. 6(C) shows a simplified diagram tracking the flow of the heated material, FIG. 9 shows a more realistic diagram of the flow of the heated material. Specifically, although FIG. 6 shows distinct circles of heated material at a given moment in time, in reality, the heated material will be a continuum. This is shown in FIG. 9, where the heated material dispersal is shown at the respective time points of t=0, 100, 200 and 300 ms.

Figure 6D:
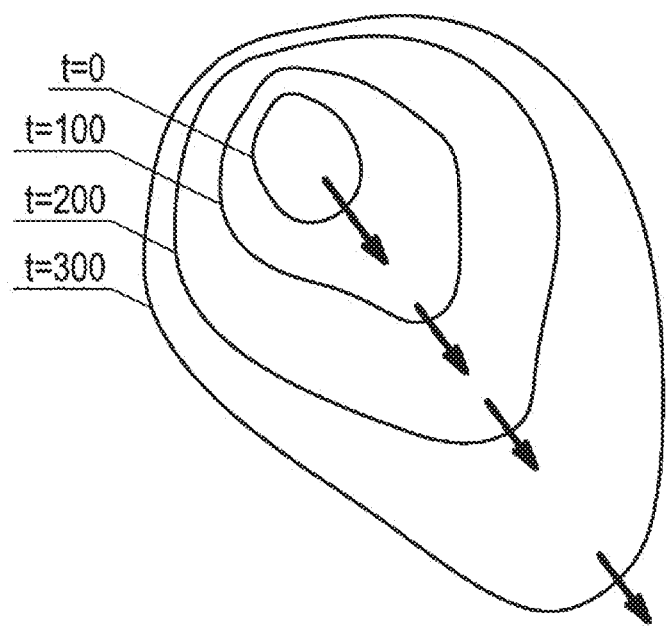

FIG. 6(D) shows a further simplified diagram at time, t=0 ms, t=100 ms, t=200 ms and t=300 ms. As can be seen, the heat pattern is applied to an area and the blood flow extends along the direction of the arrow as the blood begins to disperse from the initial source. This indicates the direction of the blood flow and from that the source of the cut or leak may be found.

Figure 6E:
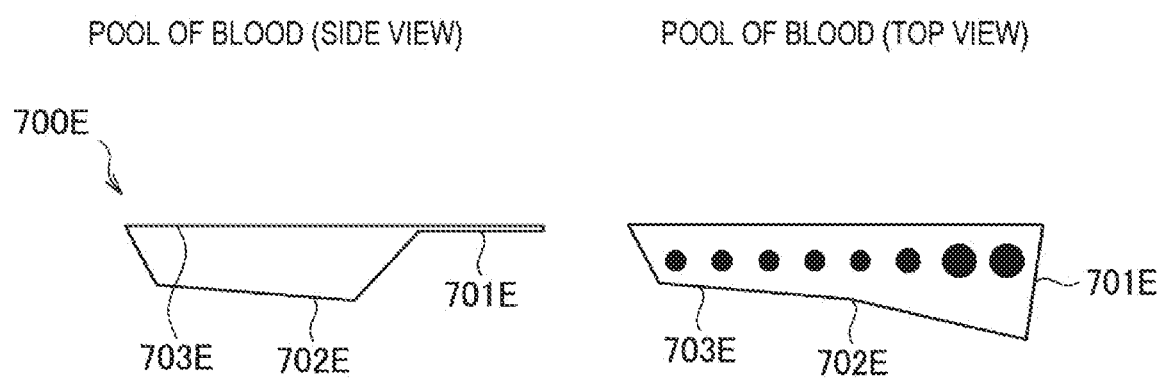

FIG. 6(E) shows a simplified diagram explaining how the variation in depth in the pool of blood may be established using the application of a heat pattern. In particular, In FIG. 6(E), the side view 700E of the pool of blood shows the topology of the tissue into which the pool of blood has formed. As can be seen from this Figure, the pool of blood is very shallow at one end 701E, is deep in the middle 702E and is slightly shallower at a second end 703E.

The heat pattern, when applied and captured by the infra-red sensor shortly after application, shows that the size of the dots is larger at the shallower end 701E compared with the size of dots at the second end 703E. The size of dots in the middle area is the smallest. This size difference is caused by the depth of blood at each location. The deeper the blood, the more heat dissipation occurs.

By identifying the relative size of the heat pattern at each location, the depth of the pool of blood can be identified at each location and the topography of the tissue under the pool can be established.

It is to be understood, that once the direction of the blood flow has been found, as the infra-red sensor is in addition to the image sensor capturing the Red, Green and Blue, (RGB) values form the endoscope, and each pixel in the infra-red sensor corresponds to a pixel in the RGB image sensor, the CCU annotates the captured RGB image with the direction of blood flow. In other words, a composite image is formed from a combination of the captured RGB image and the annotations established by the image captured by the IR sensor.

These annotations may also include the relative depth of pools of blood and the topography of the tissue under the pool of blood. This is useful information for the surgeon so may also be annotated on the RGB image.

Figure 10:
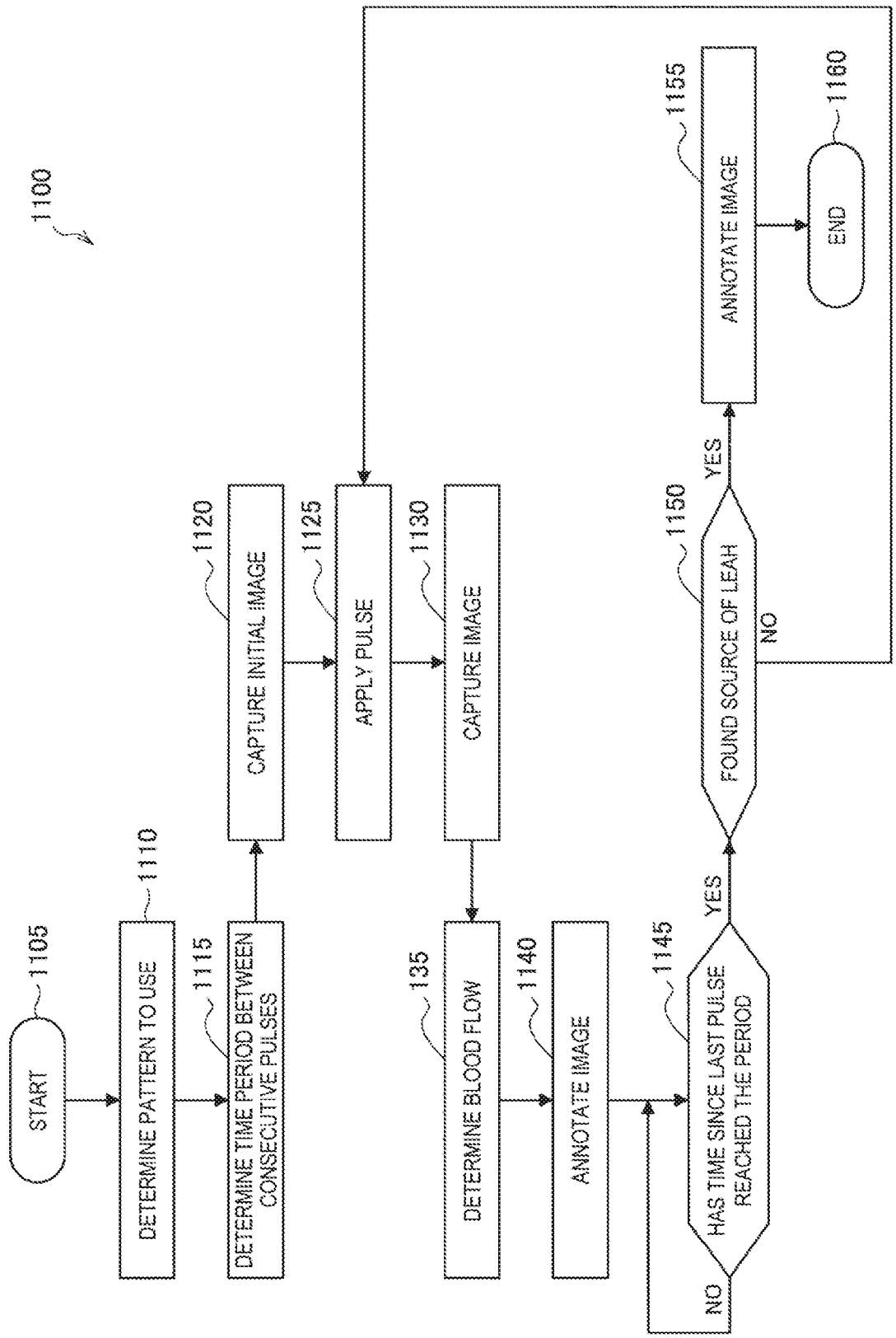
FIG. 10 shows a flow chart explaining embodiments of the disclosure.

FIG. 10 shows a flow diagram 1100 explaining the operation of embodiments of the disclosure. The process starts at 1105.

In step 1110, the pattern of infra-red light to heat the material is determined. This determination may be made by the endoscope operator or by the CCU 5039 based on, for example, the shape of the material or the amount by which the material is to be heated.

In step 1115, the time period between consecutive pulses of light is determined. As explained above, this may be determined by the speed of movement of the material for example.

In step 1120, an initial image of the material is captured. The initial image captured is in the infra-red region of light. In other words, the heat profile of the material just before the initial application of the pulse of infra-red light is captured. This provides a reference image using which the flow of heated material is established as explained later.

In step 1125, the pulse of light using the determined pattern is applied to the material.

In step 1130, an image of the material is captured. The image captured is in the infra-red region of light. In other words, the heat profile of the material just (almost immediately) after application of the pulse of infra-red light is captured. This provides a reference image using which the flow of heated material is established as explained later. This provides the heat profile of the material at the application of the pulse of infra-red light. In this first iteration of the process, this image is captured at time, t=0. A unique identifier is applied to the image captured in step 1130 uniquely identifying the pulse of light from other pulses of light.

In step 1135, the blood flow is determined. Of course, the disclosure is not limited to determining blood flow and any fluid emanating from a leak is envisaged.

The blood flow is determined by using a background subtraction algorithm on the thermal images by subtracting the heat profile of the initial image captured just before the light pulse is applied to the material (i.e. at step 1120) from the image captured just after the pulse has been applied to the material (i.e. at step 1130). The difference image is used to determine the initial blood flow.

It is envisaged that prior to the subtraction algorithm being applied, shake and camera movement is corrected using a known technique such as the mean movement of the pixels in the infra-red image. This ensures that the difference between consecutively captured images is provided by blood flow rather than camera movement.

In the initial iteration of the process of FIG. 9, the amount of blood flow will be very small due to the short period of time between step 1120 and 1130.

However, at step 1140, the image viewed by the endoscope operator and/or surgeon will be annotated as will be explained later.

In step 1145, the CCU 5039 determines whether the time elapsed since the previous pulse of light has reached the predetermined period between consecutive pulses as explained with reference to FIG. 4. In the event that the elapsed time has not reached the predetermined period, the "no" path is followed. However, in the event that the elapsed time has reached the predetermined period, the "yes" path is followed.

In step 1150, the CCU 5039 determines whether the location of the cut has been found. This will be explained later.

If the location has not been found, the "no" path is followed and the process returns to step 1125.

In the second iteration of step 1125, a second pulse of light is applied to the material. In this iteration, the pulse of light is applied 100 ms after the previous pulse is applied.

In the second iteration of step 1130, an image of the material is captured. The image captured is in the infra-red region of light. In other words, the heat profile of the material just (almost immediately) after application of the second pulse of infra-red light is captured. In this second iteration of the process, this image is captured at time, t=100. A unique identifier is applied to the image captured in step 1130 uniquely identifying the pulse of light from other pulses of light.

In the second iteration of step 1135, background subtraction is carried out on the images by subtracting the heat profile of the image captured in the first iteration of step 1130 from the image captured just after the pulse has been applied to the material in the second iteration of step 1125. The difference image is used to determine the blood flow over the last 100 ms.

Specifically, the image captured at the second iteration of step 1130 includes both the heated material from the pulse of light applied at the second iteration of step 1125 and the flow of material heated during the first iteration. Therefore, and as seen in FIG. 9, for example, the distance and dispersal of the blood over that 100 ms period is determined by detecting the distance travelled by the heated material and the amount and shape of dispersal of the heated material.

In a similar manner to the first iteration of the process, the image displayed to the endoscope operator and/or surgeon is annotated in step 1140.

Again, the process moves to step 1145 where the CCU 5039 determines whether the time elapsed since the previous pulse of light has reached the predetermined period between consecutive pulses as explained with reference to FIG. 4. In the event that the elapsed time has not reached the predetermined period, the "no" path is followed. However, in the event that the elapsed time has reached the predetermined period, the "yes" path is followed.

In a similar manner to the first iteration, in step 1150, the CCU 5039 determines whether the location of the cut has been found.

If the location has not been found, the "no" path is followed and the process returns to step 1125 for a third iteration. The process then continues until at step 1150, the source of the cut has been found.

In the event that the source of the cut has been found in step 1150, the "yes" path is followed and the image displayed to the endoscope operator and/or surgeon is annotated in step 1155. The process then ends in step 1160.

The process 1200 for determining the location of the cut (step 1150) is described with reference to FIGS. 11 and 12.

The process 1200 starts at step 1205. The process moves to step 1210, where the blood flow for each pattern element 405A-C is determined over time. In other words, the blood flow for each pattern element 405A-C since the initial image is determined. This is determined, in some embodiments, by modelling the motion of blood flow over time using a Kalman filter, for example, using the incremental motion determined in step 1135 of FIG. 10. In some embodiments, the topography of the tissue in which the cut occurs may alter the speed of heat spreading. In this case, the coarseness of the speed and direction of any stored patterns may be chosen to overcome the differences in topography. Additionally, or alternatively, a number of general patterns may be stored and the individual pattern could be constructed from a weighting of the set of general patterns.

Figure 12:
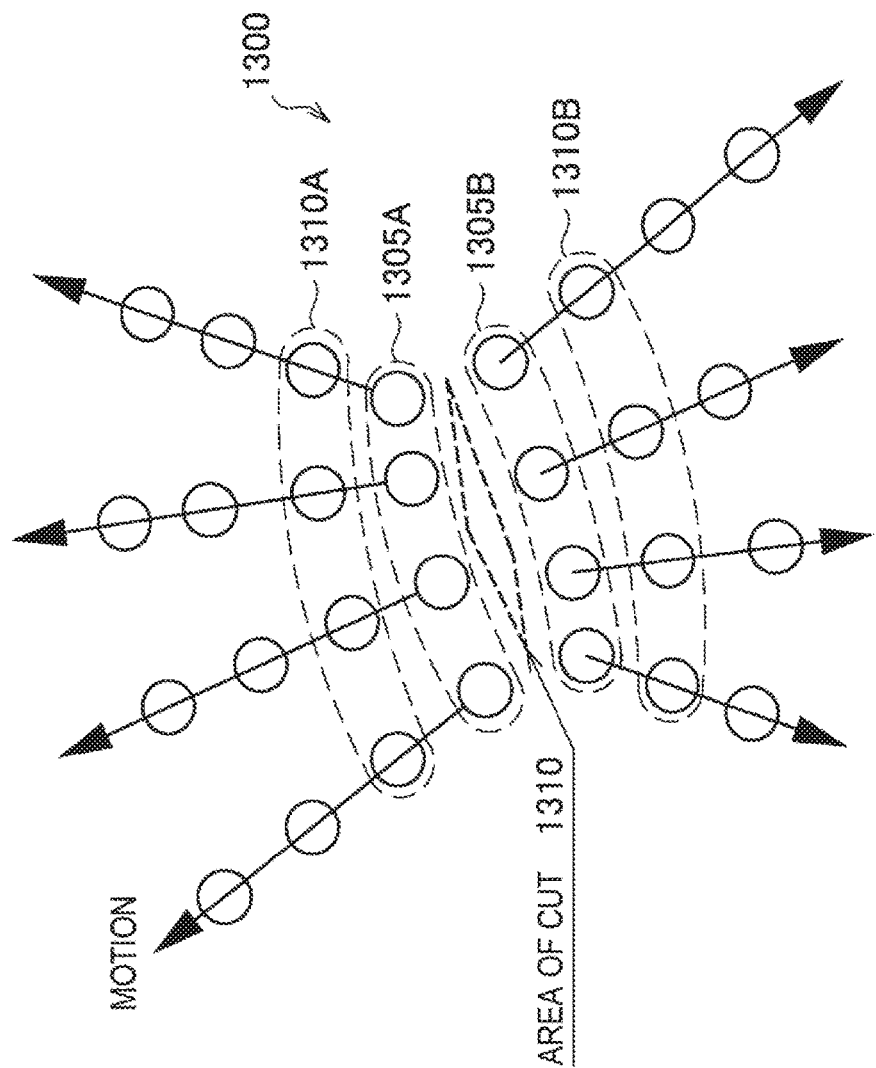
FIGS. 12 and 13 show a schematic diagram explaining identifying the source of a fluid flow.

In the example of FIG. 12, the area of the cut 1310 is shown. As is seen in FIG. 12, the blood flow 1300 is established using the technique explained in reference to FIG. 10. Specifically, the movement of the heated blood is tracked during the iterations of the process of FIG. 10 and the resultant motion of the blood shown in FIG. 12 is established. For example, during the first iteration of the process of FIG. 10, the heat pattern is applied to the blood causing the material in the circular areas shown in the dotted boundary 1305A and 1305B to be heated. During the second iteration of the process, the material heated in the first iteration has moved to dotted boundary 1310A and 1310B and the heat pattern is applied to the blood in the dotted boundary 1305A and 1305B causing localised heating of the blood defined by the circles within the dotted boundary 1305A and 1305B.

Over the various iterations of the process of FIG. 10, the blood flow can be tracked.

Figure 13:
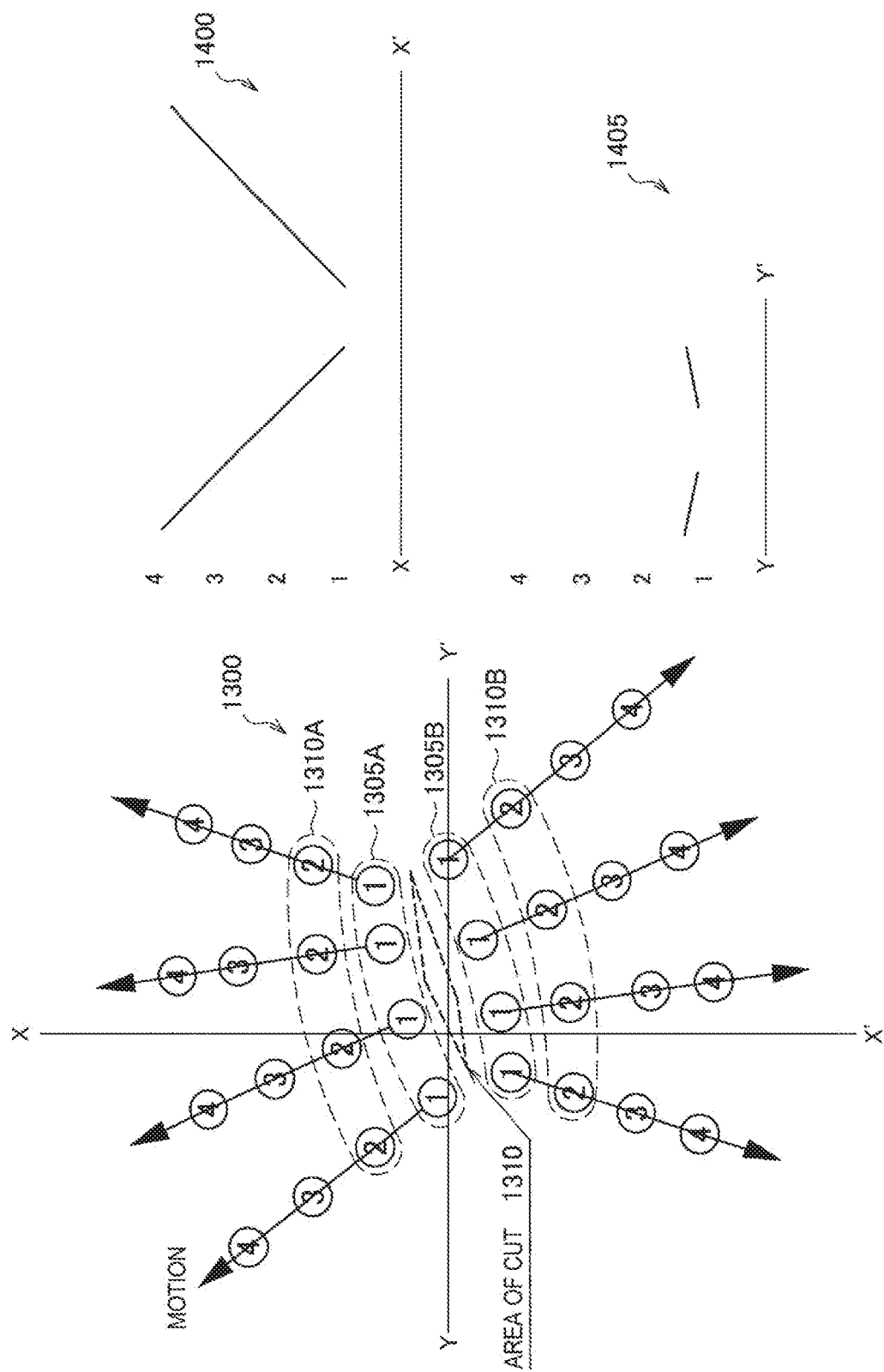

The process then moves to step 1215 where the origin of the blood flow (the cut) is calculated. This is achieved by analysing the blood flow over a predetermined period of time or number of iterations. As can be seen from FIG. 12, the area of cut 1310 has blood flowing away from the cut. A typical characteristic of a cut is that blood will either flow away from the area of the cut (as in this case) where the motion of the blood is away from the cut (where the broken tissue is higher than the surrounding tissue) or the blood will flow into the cut and collect in the cut (where the broken tissue is lower than the surrounding tissue). This is highlighted in FIG. 13, where the sections along the sections X-X' and Y-Y' in 1300 at the various iterations are shown in 1400 and 1405 respectively. Therefore, by determining the flow (motion) of the fluid, the origin of the blood, which is in this case a cut, can be found.

The process moves to step 1220 where the image is annotated identifying the position of the origin of the blood. This assists the surgeon/endoscope operator in quickly establishing the location of the cut or origin of the blood.

The process ends in step 1225.

It is envisaged that motion compensation will be carried out in order to track the pattern element evolution on the imaged surfaces over time. This is to mitigate the influence on the motion of the endoscope on the appearance of the viewed images. In order to align the captured images in which the pattern elements will be moving under the effects of blood flow etc, the appropriate transform can be calculated from the visible data from the camera, provided that the optics for both sensors are aligned and similar. A variety of operations are available to do this, which are of varying complexity and operate over different time scales:

Video stabilisation using image matching. In this process adjacent images are compared to each other and a global image transform (x and y displacement, rotation, scaling) is found that best explains these correspondences and the images are transformed (e.g. using an affine transform) to best bring them into global alignment, ignoring elements that have themselves moved. Different methods are available based on the means by which they find matching points to generate correspondences between images.

This is explained in NPL 1, the content of which is hereby incorporated by reference.

Video stabilisation using accelerometers and gyros. In this case 3 axis accelerometers and/or gyros (neither shown for brevity) are co-located with image sensor and their measurements are used to transform the images over a short period of time in order to align them. These methods can also correct for distortions produced by 'rolling shutter' cameras. This is explained in NPL 2, the content of which is hereby incorporated by reference.

More complex operations seek to generate depth maps from structure from motion algorithms. Using these to obtain projections which slightly change the viewpoint) of the camera (by obtaining new views of the generated 3D scene, a short series of images can be stabilised to appear as if the camera is not moving during the image sequence. These are explained NPL 3, the content of which is hereby incorporated by reference.

Stabilisation over longer periods of time requires smooth path generation through a series of images, but these are not applicable to the requirement here as SLUs will diffuse and disperse within at most a few seconds. An example of a suitable type of stabilisation is Microsoft® Hyperlapse®.

Figure 14:
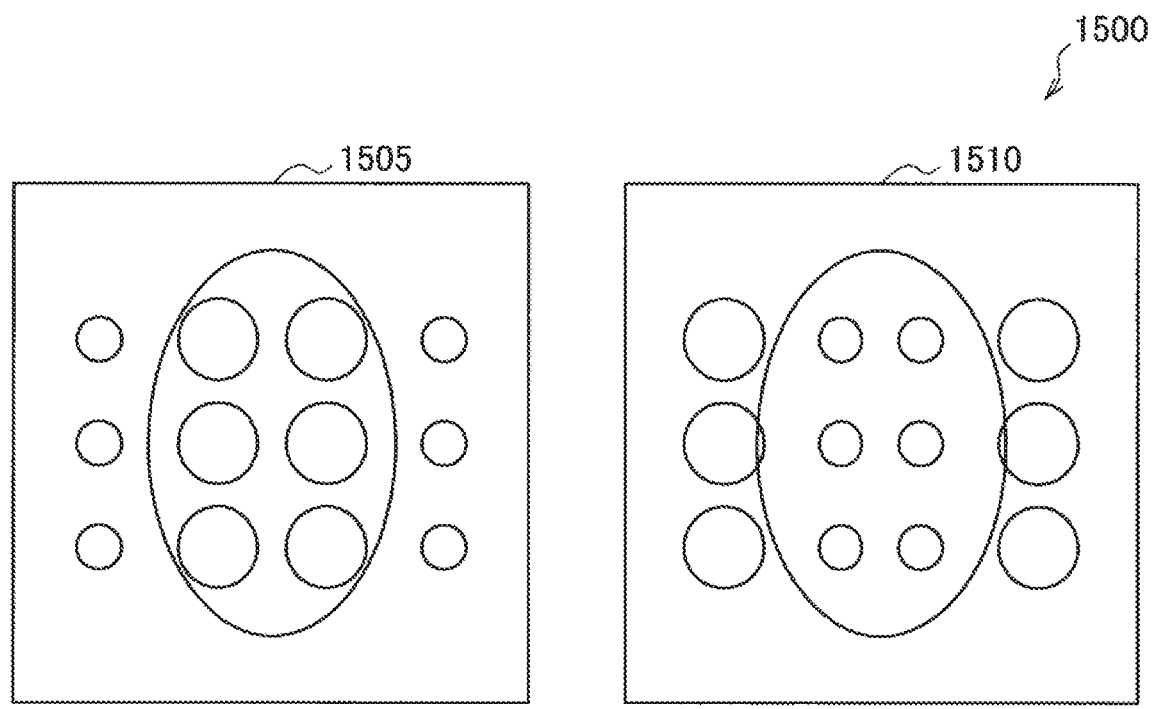
FIG. 14 shows a schematic diagram explaining further embodiments of the disclosure.

FIG. 14 shows a further embodiment of the disclosure where the pattern elements are used to improve the auto-focus of the endoscope on a particular area, for example, the origin of the fluid leak (such as the cut). In particular, the first pattern is shown in 1500 cast onto two areas of undulating tissue. In the first area 1505, as the pattern elements are of similar or substantially the same size, and because the centre pattern of pattern elements are larger than the surrounding pattern elements, this indicates that the centre pattern is closer to the endoscope than the surrounding pattern elements. Conversely, in the second area 1510, the centre pattern of pattern elements are smaller than the surrounding pattern elements. This indicates that the centre pattern is further from the endoscope than the surrounding pattern elements.

Accordingly, by iteratively adjusting the lens focus and assessing the sharpness of the pattern elements, the lens may be auto-focused.

Figure 15A:
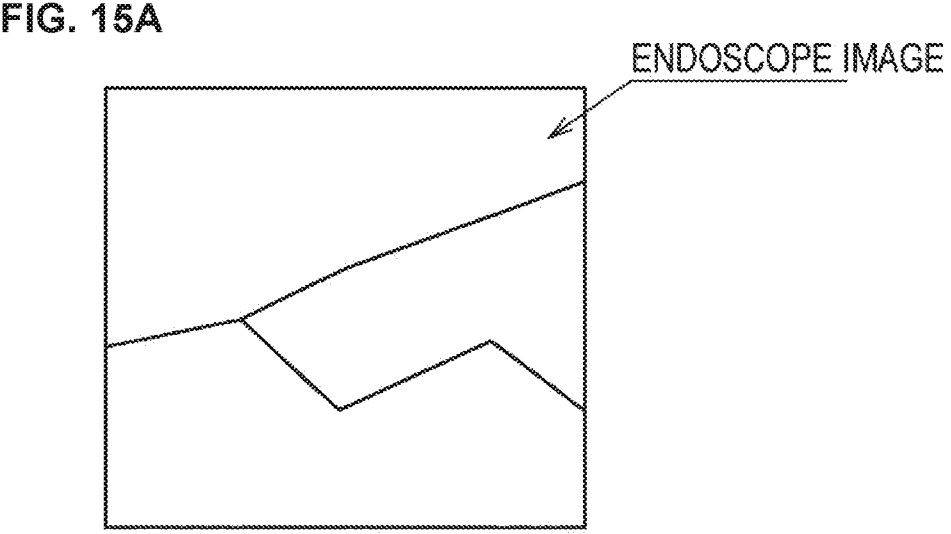
FIGS. 15A-15C show the annotations that may be applied to the endoscope image.
Figure 15B:
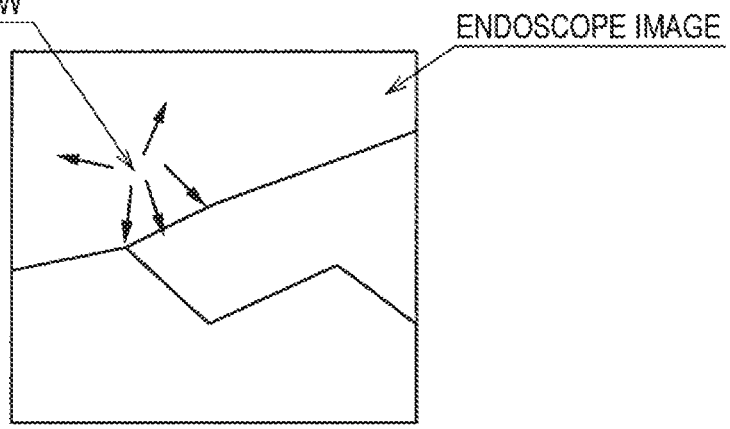
Figure 15C:
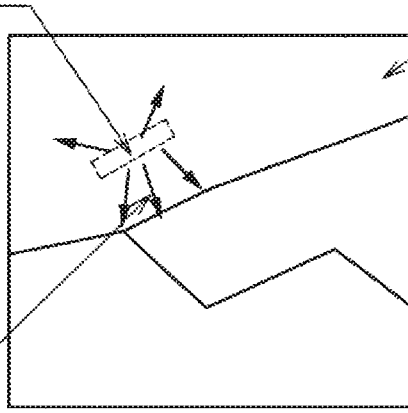

FIGS. 15A-15C show the annotations that may be applied to the endoscope image. Specifically, in FIG. 15A, an endoscope image is shown without any annotations assisting the endoscope operator or surgeon. In FIG. 15B, the endoscope image including annotations of the blood flow is shown. This is typically the output from step 1140 of FIG. 10. In FIG. 15C, the endoscope image including annotations of the blood flow and origin of leak (for example, cut). In this case, in addition to the blood flow being shown, the cut is also shown. Of course, it is envisaged that the cut may be shown without the blood flow.

Material Differentiation

In embodiments of the disclosure, the pattern elements may be used to differentiate between materials found within the patient (or object for a non-medical endoscopy scenario).

Use to Find Mist

Pattern elements formed on mist are likely to be less uniform than those formed on liquid or solid (i.e. the shape of the pattern element itself is likely to be less uniform). Also mist particles are more likely to be mobile than liquid or solid particles, hence the diffusion of heat within the mist is likely to be noticeably different to the heat dissipation within the pattern element formed in liquid or solids. Accordingly, by analysing the uniformity of the pattern element imparted onto the material and/or the heat dissipation of the heated material, the presence of mist may be established.

Use to Find Artificial Materials

During endoscopic surgery objects are used made from non-organic materials (e.g. tools for surgery). Where these materials display different thermal properties to the organic material of the patient, embodiment methods can be used to detect them.

For example, heat dissipation in static liquid is likely to be approximately uniform in all directions within the liquid, governed by Brownian motion. However a non-organic object may well have a different thermal conductivity than the organic material typically found in the endoscopic image. If this thermal conductivity is sufficiently different, the various materials may be differentiated. Also the other material may have some particular structure (for example be laminated) that effects the way heat is propagated through it, and by detecting heat flow of this structure (e.g. the direction that heat propagates) then this may be used as a differentiating factor. The technique for detecting the heat propagation is as described with reference to FIG. 10.

Use to Distinguish Between Materials

Referring to FIG. 16A, an endoscopic view 2000 is shown. In this view 2000, veins 2010 and 2015 are seen connected to muscle 2005. The muscle fibre is orientated in the direction of arrow 2220. In vein 2010, blood flows towards muscle 2005. In vein 2015, blood flows in the directions indicated by arrow 20151 and arrow 20151.

Figure 16B:
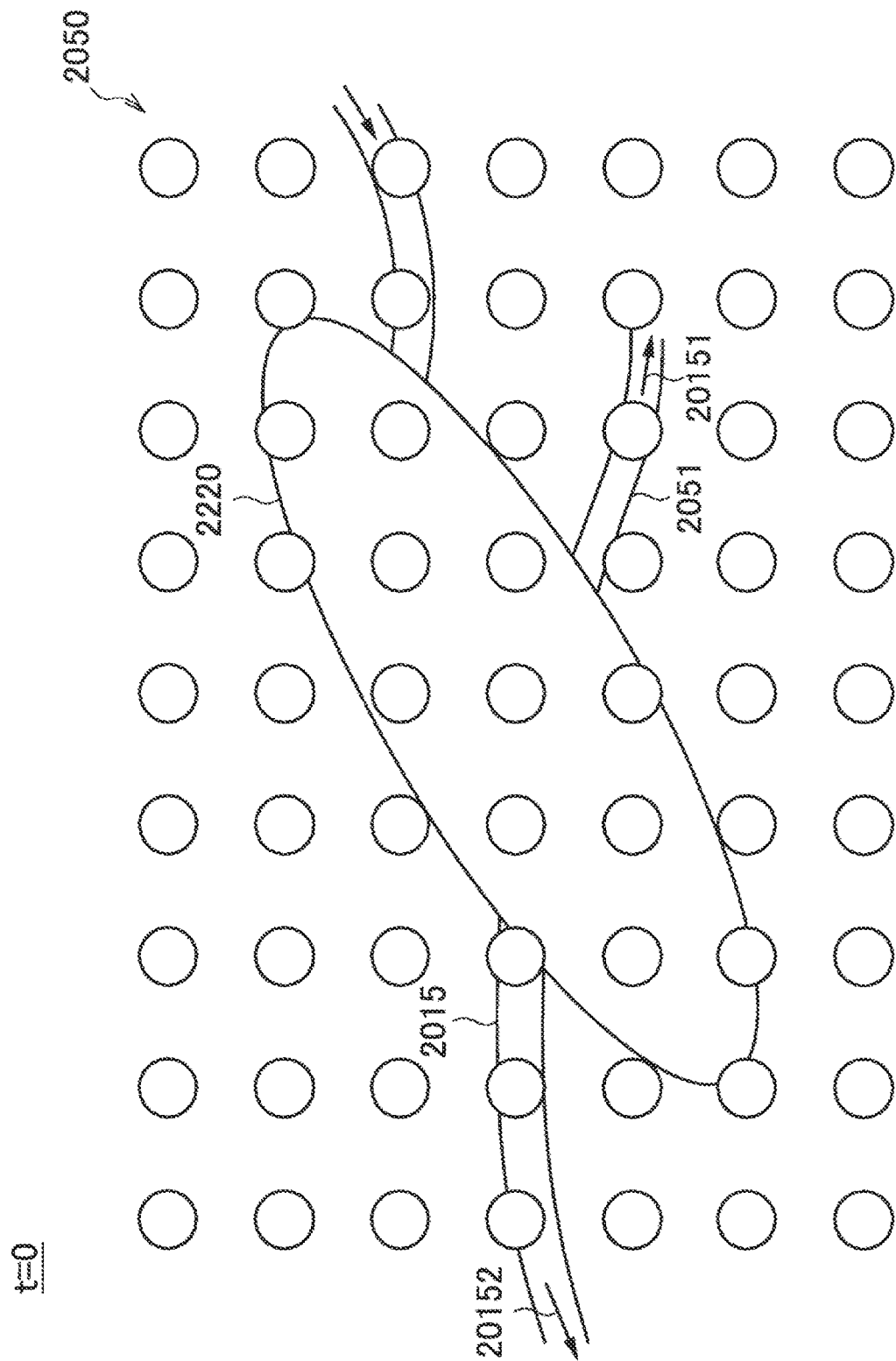

FIG. 16B shows the endoscopic view of FIG. 16A at the moment (i.e. at t=0) that the pattern of heat is applied. In other words, the endoscopic view 2050 of FIG. 16B shows the endoscopic view of FIG. 16A when the heating pattern is applied. In this case, the heating pattern is composed of dots 2055 similar to those shown in FIG. 3A.

FIG. 16C shows the endoscopic view of FIG. 16B a time interval after application of the heat pattern. In the specific embodiment of FIG. 16C, the time interval is 100 ms later. As can be seen from FIG. 16C, the heat pattern in the muscle 2005 is diffused along the length of the muscle fibre. Additionally, the heat pattern over the veins is diffused along the length of the veins. In particular, the heat pattern over vein 2010 diffuses in the direction of the muscle. This indicates the blood flow of that particular vein. Similarly, in vein 2015, the heat patterns 2015A and 2015B are both diffused away from the muscle.

It should be noted here that the amount of diffusion over that time interval indicates the type of material onto which the heat pattern is placed. Specifically, the amount of diffusion in the muscle is less than the amount of diffusion in the veins. This is because the heat dissipation characteristics of muscle are different to those of blood. This rate of diffusion is measured by the control circuitry and compared with stored values of diffusion for various materials found in the patient. These stored values will be obtained during clinical trials and stored in the storage device or obtained over the network.

By comparing the measured rates of diffusion against the values obtained during clinical trials, it is possible to identify the type of material onto which the heat pattern has been provided. In addition, as exemplified in FIG. 17, the rate of diffusion of the blood may also vary depending on the volume of blood passing through the veins at any given time. For example, if the vein was a capillary, the amount of blood flow, and thus heat dissipation, would be small as the heat is not dissipated by the blood. However, if the vein was in fact an artery, where the rate of blood flow is high compared with a vein, the heat dissipation would be high because the heat will be dissipated by the blood. This indicates to the surgeon a risk of any cut; if a capillary is cut, the risk to the patient is low, however, in the event of a cut to an artery, the risk to the patient is high.

Moreover, by establishing the rate of blood flow in a material, it is possible to detect cancers and tumours. This is because the rate of blood flow in cancerous material and tumours is high compared with non-cancerous materials. In other words, as the blood flow through cancerous material and tumours is higher than to non-cancerous material and tumours, the rate of heat dissipation would be higher than expected. This can be measured in two ways. Firstly, the heating pattern may be applied to a known non-cancerous part of the tissue to establish the rate of heat dissipation and compare this rate of heat dissipation to the potentially cancerous area. Secondly, the rate of heat dissipation in the potentially cancerous area may be compared to stored values.

In summary, therefore, by measuring the rate of heat dissipation, and comparing the rate of heat dissipation with stored reference rates obtained either prior to the surgery or medical procedure or during the surgery of medical procedure, the type of material may be established. In addition, by identifying the direction of the dissipation established from the shape of the heat dissipation, it is possible to identify the orientation of the material and even the direction of blood flow. Further, by identifying the rate of heat dissipation, it is possible to establish whether an area of tissue is cancerous.

Figure 17:
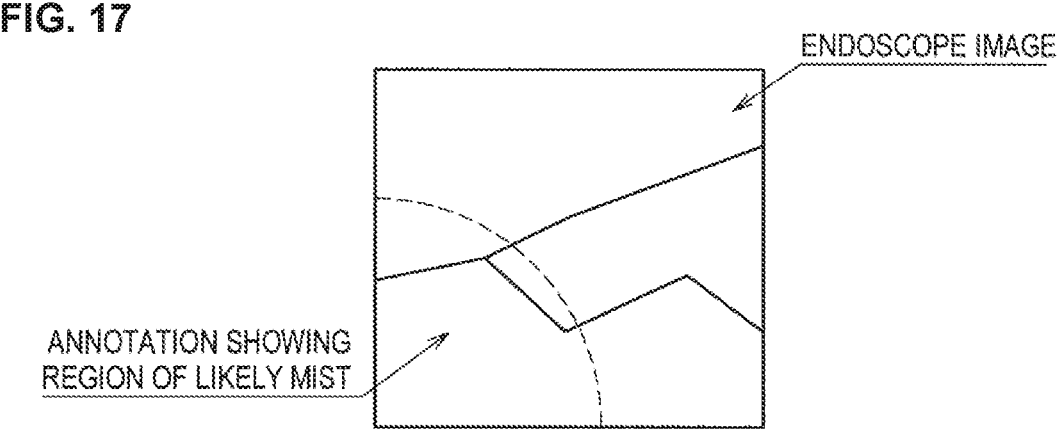
FIGS. 17 to 19 shows schematic diagrams explaining annotating images according to embodiments of the disclosure.
Figure 18:
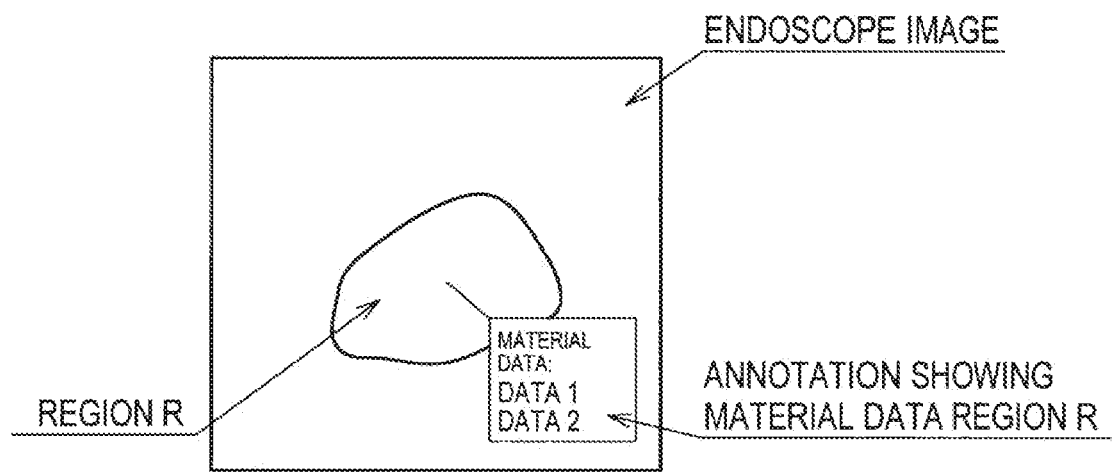
Figure 19:
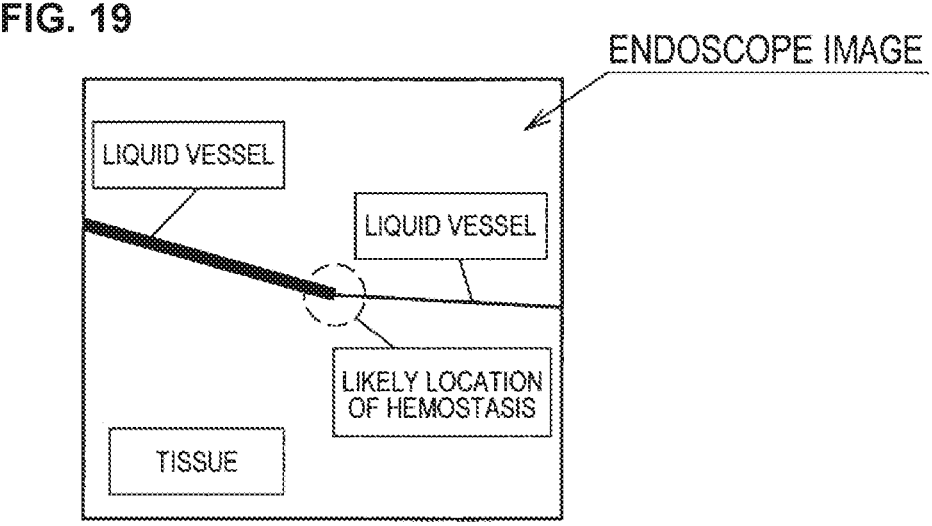

FIGS. 17 and 18 shows example annotations that may be applied to the endoscope image. Further, in FIG. 19, the various different materials may also be annotated on the endoscope image. This may include areas of blood flow, directions of blood flow, and even possibly cancerous material to direct the surgeon to an area to perform a biopsy or the like. Further, by identifying the rate and direction of blood flow to the area, the surgeon will know the patient risk in performing such a biopsy.

Figure 11:
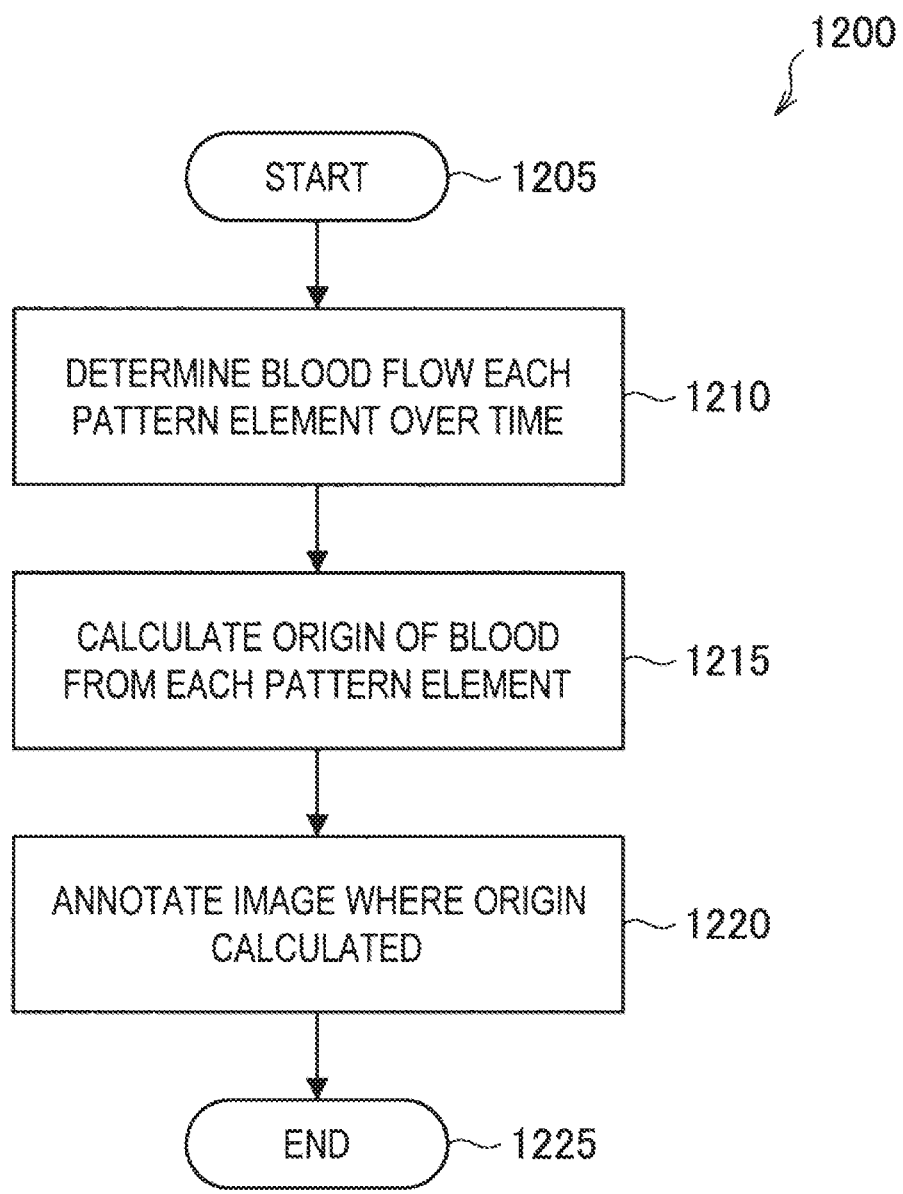
FIG. 11 shows a flow chart explaining embodiments of the disclosure.

Although the above describes the process of FIG. 10 and FIG. 11 being carried out in the CCU 5039, the disclosure is not so limited. For example, one or more of the processes or parts of the processes may be carried out in the camera head controlling unit 5015.

Although the above describes the light source as being a VCSL, the disclosure is not limited to this. For example, the light source may produce only light in the Infra-Red spectrum, or, as described above, in both the Infra-Red and visible light spectrum, or in the visible light spectrum only.

Indeed, although the above describes the light source as providing the heat to locally heat the material, the light source may be used to provide light in the Infra-Red spectrum to locally heat the material and, when not heating the material, may be used to illuminate the area with visible light to assist the endoscope operator and/or surgeon. This reduces the number of light sources required in the endoscope and thus the size, cost and complexity of the endoscope device.

Moreover, the light source may produce light which is coherent (such as LASER light) or non-coherent (such as that produced by a Light Emitting Diode). The light source may also produce light in various spectra. For example, the light source may produce a single wavelength (or narrow band) of light such as green light which has high absorption by the human body. Alternatively, the light source may be tuned to different colours of light. In this case, as the absorption of the light by the material varies, the time to heat the material by a given amount will vary depending on the material and the wavelength of light. Accordingly, the wavelength of light used to produce the heating pattern elements may be stored in the table of FIG. 4.

Although the above has been used to determine the source of a cut, for example, the disclosure is not so limited. By determining the flow of blood in tissue, the vascularity and perfusion within the tissue may also be deduced by determining whether the blood supply to a certain region is poor or excessive.

Although the above has been mentioned with respect to endoscopy, the disclosure is not so limited. In fact, embodiments of the disclosure are applicable to any kind of surgical device or medical imaging device. Examples include, but are not limited to, surgical microscopy, for use in procedures such as neurosurgery, or debridement of a wound and other medical imaging devices such as those used in hysteroscopy.

Various embodiments of the present disclosure are defined by the following numbered clauses:

1. A medical imaging system comprising an heating element configured to apply at least one heating pattern element to a material to locally heat the material; a sensor configured to capture the position of the heated material a predetermined time after the application of the heating pattern element; and circuitry configured to determine the change of the heating pattern applied to the material based upon the captured position of the heated material after the predetermined time.

2. A medical imaging system according to clause 1, wherein the heating element is further configured to apply a plurality of heating pattern elements arranged as a heating pattern to the material.

3. A medical imaging system according to clause 2, wherein each heating pattern element with the heating pattern is substantially the same size.

4. A medical imaging system according to clause 1 to 3, wherein the heating element is configured to emit infra-red radiation to heat the material.

5. A medical imaging system according to clause 3, wherein the heating element is further configured to emit light in the visible spectrum.

6. A medical imaging system according to clause 1 to 5, wherein the heating element is a laser light emitting device.

7. A medical imaging system according to clause 6, wherein the heating element is a Vertical Cavity Surface Emitting Laser disposed on a distal end of the endoscope device.

8. A medical imaging system according to clause 1 to 7, wherein the circuitry is configured to determine the movement of the material by comparing the image captured after the predetermined time with a previously captured image.

9. A medical imaging system according to clause 1 to 8, wherein the circuitry is configured to apply image stabilisation to the image prior to capture by the sensor.

10. A medical imaging system according to clause 1 to 9, wherein the material is a fluid and the circuitry is configured to determine the movement of the fluid on the basis of the change of the heating pattern over a defined period of time.

11. A medical imaging system according to clause 10, wherein the circuitry is configured to determine the source of the fluid on the basis of the movement.

12. A medical imaging system according to clause 1 to 11, wherein the circuitry configured to determine a diffusion rate of the heating based on the change of the heating pattern.

13. A medical imaging system according to clause 12, wherein the circuitry configured to determine a characteristic of the material based on the diffusion rate.

14. A medical imaging system according to clause 1 to 13, wherein the circuitry is configured to annotate the captured image with the movement of the material and to display the annotated image.

15. A medical imaging system according to clause 10 to 14, wherein the circuitry is configured to annotate the captured image with the source of the fluid and to display the annotated image.

16. A medical imaging system according to clause 2, further comprising a lens arrangement and the circuitry is configured to adjust the focal distance of the lens arrangement such that a subset of the plurality of heating elements is in focus.

17. A medical imaging system according to clause 1 to 16, the system further comprising an image sensor for imaging endoscope image comprising at least red, green and blue colour components.

18. A medical imaging system according to clause 1 to 17, wherein the sensor is configured to detect an infra-red wavelength light.

19. A medical imaging system according to clause 18, wherein the sensor is configured to detect the visible wavelength light.

20. A method in a medical imaging system, the method comprising applying at least one heating pattern element to a material to locally heat the material; capturing the position of the heated material a predetermined time after the application of the heating pattern element; and determining the change of the heating pattern applied to the material based upon the captured position of the heated material after the predetermined time.

21. A computer program product comprising computer readable instructions which, when loaded onto a computer, configures the computer to perform a method according to clause 20.

Obviously, numerous modifications and variations of the present disclosure are possible in light of the above teachings. It is therefore to be understood that within the scope of the appended claims, the disclosure may be practiced otherwise than as specifically described herein.

In so far as embodiments of the disclosure have been described as being implemented, at least in part, by software-controlled data processing apparatus, it will be appreciated that a non-transitory machine-readable medium carrying such software, such as an optical disk, a magnetic disk, semiconductor memory or the like, is also considered to represent an embodiment of the present disclosure.

It will be appreciated that the above description for clarity has described embodiments with reference to different functional units, circuitry and/or processors. However, it will be apparent that any suitable distribution of functionality between different functional units, circuitry and/or processors may be used without detracting from the embodiments.

Described embodiments may be implemented in any suitable form including hardware, software, firmware or any combination of these. Described embodiments may optionally be implemented at least partly as computer software running on one or more data processors and/or digital signal processors. The elements and components of any embodiment may be physically, functionally and logically implemented in any suitable way. Indeed the functionality may be implemented in a single unit, in a plurality of units or as part of other functional units. As such, the disclosed embodiments may be implemented in a single unit or may be physically and functionally distributed between different units, circuitry and/or processors.

Although the present disclosure has been described in connection with some embodiments, it is not intended to be limited to the specific form set forth herein. Additionally, although a feature may appear to be described in connection with particular embodiments, one skilled in the art would recognize that various features of the described embodiments may be combined in any manner suitable to implement the technique.

The invention claimed is:

1. A medical imaging system comprising:
a heating element configured to apply at least one heating pattern element to a material to locally heat material at a first time;
a sensor configured to capture a first heating pattern of the heated material at the first time and a second heating pattern of the heated material at a second time that is a predetermined time after the application of the heating pattern element; and
circuitry configured to:
determine changes between the first and second heating patterns, and
on condition that the heated material includes a fluid, determine a flow direction of the fluid based on the changes.

2. A medical imaging system according to claim 1, wherein the heating element is further configured to apply a plurality of heating pattern elements arranged as a heating pattern to the material.

3. A medical imaging system according to claim 2, wherein each heating pattern element of the heating pattern is substantially the same size.

4. A medical imaging system according to claim 1, wherein the heating element is configured to emit infra-red radiation to heat the material.

5. A medical imaging system according to claim 4, where the heating element is further configured to emit light in the visible spectrum.

6. A medical imaging system according to claim 1, wherein the heating element is a laser light emitting device.

7. A medical imaging system according to claim 6, wherein the heating element is a Vertical Cavity Surface Emitting Laser disposed on a distal end of an endoscope device.

8. A medical imaging system according to claim 1, wherein the circuitry is configured to determine the movement of the material by comparing the image captured after the predetermined time with a previously captured image.

9. A medical imaging system according to claim 1, wherein the circuitry is configured to determine a source of the fluid on the basis of the changes.

10. A medical imaging system according to claim 1, wherein the circuitry configured to determine a diffusion rate of the heating based on the change of the heating pattern.

11. A medical imaging system according to claim 10, wherein the circuitry configured to determine a characteristic of the material based on the diffusion rate.

12. A medical imaging system according to claim 1, wherein the circuitry is configured to annotate the captured image with the direction of flow of the fluid and to display the annotated image.

13. A medical imaging system according to claim 9, wherein the circuitry is configured to annotate the captured image with the source of the fluid and to display the annotated image.

14. A medical imaging system according to claim 2, further comprising a lens arrangement and the circuitry is configured to adjust the focal distance of the lens arrangement such that a subset of the plurality of heating elements are in focus.

15. A medical imaging system according to claim 1, the system further comprising an image sensor for imaging endoscope image comprising at least red, green and blue colour components.

16. A medical imaging system according to claim 1, wherein the sensor is configured to detect an infra-red wavelength light.

17. A medical imaging system according to claim 16, wherein the sensor is configured to detect the visible wavelength light.

18. A method in a medical imaging system, the method comprising:
　applying at least one heating pattern element to a material to locally heat material at a first time;
　capturing a first heating pattern of the heated material at the first time and a second heating pattern of the heated material at a second time that is a predetermined time after the application of the heating pattern element; and
　determining changes between the first and second heating patterns, and
　on condition that the heated material includes a fluid, determining a flow direction of the fluid based on the changes.

19. A non-transitory recording medium storing a computer program comprising computer readable instructions which, when loaded onto a computer, configures the computer to perform a method according to claim 18.

20. A medical imaging system according to claim 11, wherein the circuitry configured to determine whether the material is a fluid or not based on the diffusion rate.

21. A medical imaging system according to claim 20, wherein the circuitry configured to determine a flow rate of the fluid based on the diffusion rate.

* * * * *